US010610378B2

United States Patent
Piron et al.

(10) Patent No.: US 10,610,378 B2
(45) Date of Patent: *Apr. 7, 2020

(54) FEEDBACK FOR PROVIDING ARTIFICIAL BONE FLAP

(71) Applicant: SYNAPTIVE MEDICAL (BARBADOS) INC., Bridgetown (BB)

(72) Inventors: Cameron Piron, Toronto (CA); Murugathas Yuwaraj, Toronto (CA); Joshua Lee Richmond, Toronto (CA); Gal Sela, Toronto (CA)

(73) Assignee: SYNAPTIVE MEDICAL (BARBADOS) INC., Bridgetown (BB)

( * ) Notice: Subject to any disclaimer, the term of this patent is extended or adjusted under 35 U.S.C. 154(b) by 0 days.

This patent is subject to a terminal disclaimer.

(21) Appl. No.: 15/504,783

(22) PCT Filed: Mar. 17, 2015

(86) PCT No.: PCT/CA2015/050196
§ 371 (c)(1),
(2) Date: Feb. 17, 2017

(87) PCT Pub. No.: WO2016/026029
PCT Pub. Date: Feb. 25, 2016

(65) Prior Publication Data
US 2017/0231771 A1    Aug. 17, 2017

(30) Foreign Application Priority Data
Aug. 20, 2014    (WO) ............... PCT/CA2014/050798

(51) Int. Cl.
A61F 2/46        (2006.01)
A61B 5/00        (2006.01)
(Continued)

(52) U.S. Cl.
CPC .......... *A61F 2/4601* (2013.01); *A61B 5/0035* (2013.01); *A61B 5/0037* (2013.01);
(Continued)

(58) Field of Classification Search
None
See application file for complete search history.

(56) References Cited

U.S. PATENT DOCUMENTS 8,635,082 B2    1/2014 Woods et al.
2003/0216669 A1  11/2003 Lang et al.
(Continued)

FOREIGN PATENT DOCUMENTS

EP        2754419 A2        7/2014
WO    WO 2013/013170 A1    1/2013
WO    WO 2014/145267 A1    9/2014

*Primary Examiner* — Samuel S Hanna
(74) *Attorney, Agent, or Firm* — Ridout & Maybee LLP

(57) ABSTRACT

Methods and systems for providing feedback to guide selection of an artificial bone flap. A user interface for planning a neurosurgical procedure is provided, the neurosurgical procedure including closing of an opening in a portion of a patient's skull using an artificial bone flap. 3D dimensions of the opening are determined using at least pre-operative three-dimensional (3D) imaging data. One or more parameters for selecting an artificial bone flap are determined, where the one or more parameters are based on at least the 3D dimensions of the opening. Output indicating one or more recommended available artificial bone flaps suitable for closing the opening is provided, the recommendation being based on the determined one or more parameters.

14 Claims, 13 Drawing Sheets

(51) Int. Cl.
    *A61B 5/055*     (2006.01)
    *A61B 5/06*     (2006.01)
    *A61B 5/107*     (2006.01)
    *A61B 6/03*     (2006.01)
    *A61F 2/28*     (2006.01)
    *A61B 34/00*     (2016.01)
    *A61B 34/20*     (2016.01)
    *G05B 19/4097*     (2006.01)
    *A61F 2/30*     (2006.01)
    *A61B 34/10*     (2016.01)
    *A61B 6/00*     (2006.01)
    *A61B 8/08*     (2006.01)
    *A61B 17/00*     (2006.01)
    *A61B 17/064*     (2006.01)
    *A61B 17/86*     (2006.01)
    *A61B 90/00*     (2016.01)

(52) U.S. Cl.
CPC .......... *A61B 5/0042* (2013.01); *A61B 5/0066* (2013.01); *A61B 5/055* (2013.01); *A61B 5/064* (2013.01); *A61B 5/1072* (2013.01); *A61B 5/1079* (2013.01); *A61B 6/03* (2013.01); *A61B 6/032* (2013.01); *A61B 6/037* (2013.01); *A61B 6/505* (2013.01); *A61B 6/5229* (2013.01); *A61B 8/0841* (2013.01); *A61B 17/00491* (2013.01); *A61B 17/0642* (2013.01); *A61B 17/86* (2013.01); *A61B 34/00* (2016.02); *A61B 34/10* (2016.02); *A61B 34/20* (2016.02); *A61F 2/28* (2013.01); *A61F 2/2875* (2013.01); *A61F 2/30942* (2013.01); *A61F 2/46* (2013.01); *G05B 19/4097* (2013.01); *A61B 2034/104* (2016.02); *A61B 2034/105* (2016.02); *A61B 2034/107* (2016.02); *A61B 2034/108* (2016.02); *A61B 2034/2051* (2016.02); *A61B 2034/2055* (2016.02); *A61B 2034/2065* (2016.02); *A61B 2034/2068* (2016.02); *A61B 2090/363* (2016.02); *A61B 2090/365* (2016.02); *A61B 2090/3735* (2016.02); *A61F 2002/2835* (2013.01); *A61F 2002/30948* (2013.01); *A61F 2002/4632* (2013.01); *G05B 2219/35134* (2013.01); *G05B 2219/49007* (2013.01)

(56) References Cited

U.S. PATENT DOCUMENTS

| | | |
|---|---|---|
| 2007/0179626 A1 | 8/2007 | de la Barrera et al. |
| 2011/0087332 A1* | 4/2011 | Bojarski .............. A61B 17/155 623/20.32 |
| 2012/0215322 A1* | 8/2012 | Liao ...................... A61F 2/2875 623/23.72 |
| 2013/0103375 A1* | 4/2013 | Chen ...................... G06T 19/00 703/11 |
| 2013/0203031 A1 | 8/2013 | Mckinnon et al. |
| 2014/0003695 A1* | 1/2014 | Dean ...................... G06T 7/0012 382/131 |

* cited by examiner

FEEDBACK FOR PROVIDING ARTIFICIAL BONE FLAP

CROSS-REFERENCE TO RELATED APPLICATIONS

The present disclosure claims priority from PCT Application No. PCT/CA2014/050798, filed Aug. 20, 2014, the entirety of which is hereby incorporated by reference.

FIELD

The present disclosure relates to methods and systems for providing feedback suitable for selection, modification and/or fabrication of an artificial bone flap. More particularly, the present disclosure relates to methods and systems suitable for use in craniotomy procedures, including image-guided medical procedures and planning for such procedures.

BACKGROUND

Craniotomy procedures involve the creation of an opening in a patient's skull, in order to access the patient's brain. The closure of this opening typically involves replacing the bone flap, which was removed to create the opening, back into the opening. However, the need to preserve the bone flap may be problematic as the bone flap may have been fractured or otherwise damaged during removal and/or may not have been removed as a single piece. Any structural damage to the bone flap may compromise patient healing. Inadvertent contamination of the bone flap may also occur during the procedure, which, if not properly detected and treated, may lead to infection of the patient.

Further, craniectomy procedures typically do not involve preservation of the bone flap. Thus, it may be useful to provide a way to provide information to select, modify and/or fabricate an artificial bone flap to close the craniectomy opening.

SUMMARY

In some example embodiments, the present disclosure provides a method for calculating, in a processor, dimensions for fabricating an artificial bone flap, the method may include: obtaining, using a portable three-dimensional (3D) scanner, intra-operative data indicating dimensions of an opening in a portion of the patient's skull, the intra-operative data including a 3D surface scan of the portion of the patient's skull including the opening and including a first plurality of reference points located on or near the patient; obtaining a 3D reference image of at least the portion of the patient's skull without the opening, the 3D reference image including a second plurality of reference points that at least partly overlap with the first plurality of reference points; calculating 3D dimensions of the opening using the intra-operative data, the intra-operative data being registered to the reference image on the basis of the overlapping reference points; and storing, in a memory in communication with the processor, the calculated 3D dimensions for fabricating the artificial bone flap by a fabrication system.

In some example embodiments, the present disclosure provides a method for calculating, in a processor, dimensions for fabricating an artificial bone flap, the method may include: obtaining intra-operative data indicating dimensions of an opening in a portion of the patient's skull; obtaining a three-dimensional (3D) reference image of at least the portion of the patient's skull without the opening; calculating 3D dimensions of the opening using the intra-operative data, the intra-operative data being registered to the reference image; and storing, in a memory in communication with the processor, the calculated 3D dimensions for fabricating the artificial bone flap by a fabrication system.

In some example embodiments, the present disclosure provides a system for calculating dimensions for fabricating an artificial bone flap, the system comprising a processor configured to execute instructions to cause the system to carry out the methods described herein.

In some example embodiments, the present disclosure provides a computer readable product for calculating dimensions for fabricating an artificial bone flap, the computer readable product comprising computer-executable instructions that, when executed, causes a computer system to carry out the methods described herein.

In some example embodiments, the present disclosure provides a method, in a processor, for providing feedback to guide selection of an artificial bone flap, the method may include: obtaining, using a portable three-dimensional (3D) scanner, intra-operative data indicating dimensions of an opening in a portion of a patient's skull, the intra-operative data including a 3D surface scan of the portion of the patient's skull including the opening and including a first plurality of reference points located on or near the patient; obtaining a 3D reference image of at least the portion of the patient's skull without the opening, the 3D reference image including a second plurality of reference points that at least partly overlap with the first plurality of reference points; calculating 3D dimensions of the opening using the intra-operative data, the intra-operative data being registered to the reference image on the basis of the overlapping reference points; and providing output indicating one or more recommended available artificial bone flaps suitable for closing the opening, based on the calculated 3D dimensions of the opening.

In some examples, the method may include: searching a database of available artificial bone flaps to identify the one or more recommended available artificial bone flaps, by determining one or more available artificial bone flaps having 3D dimensions closest to the calculated 3D dimensions of the opening; and providing as the output identification of the one or more recommended available artificial bone flaps from the database.

In some examples, the method may include: obtaining 3D dimensions of a selected artificial bone flap; comparing the 3D dimensions of the selected artificial bone flap to the calculated 3D dimensions of the opening; and providing output indicating one or more recommended dimensional modifications to the selected artificial bone flap, based on any differences between the 3D dimensions of the selected artificial bone flap and the calculated 3D dimensions of the opening.

In some examples, the output may include one or more recommendations for manually shaping the selected artificial bone flap to more closely approximate the calculated 3D dimensions of the opening.

In some examples, the output may include one or more recommendations for one or more fasteners for fixing the artificial bone flap over the opening. The one or more fasteners may include one or more of: a bone screw, a bone staple or a bone adhesive, among others.

In some example embodiments, the present disclosure provides a method, in a processor, for providing feedback to guide selection of an artificial bone flap, the method including: providing a user interface for planning a neurosurgical procedure, the neurosurgical procedure including closing of an opening in a portion of a patient's skull using the artificial bone flap; using at least pre-operative three-dimensional (3D) imaging data, determining 3D dimensions of the opening; determining one or more parameters for selecting an artificial bone flap for closing the opening, the one or more parameters being based on at least the 3D dimensions of the opening; and providing output indicating one or more recommended available artificial bone flaps suitable for closing the opening, based on the determined one or more parameters.

In some examples, the method may include calculating at least one of: a bone density in a vicinity of the opening or a bone structural integrity in the vicinity of the opening, using at least the pre-operative 3D imaging data.

In some examples, the method may include determining one or more locations in the vicinity of the opening suitable for attaching a bone flap fastener, based on the calculation of the bone density and/or bone structural integrity in the vicinity of the opening; and providing output indicating the one or more locations for attaching the bone flap fastener.

In some example embodiments, the present disclosure provides system for providing feedback for selection of an artificial bone flap, the system comprising a processor configured to execute instructions to cause the system to carry out the methods described herein.

In some example embodiments, the present disclosure provides a computer readable product for providing feedback for selection of an artificial bone flap, the computer readable product comprising computer-executable instructions that, when executed, causes a computer system to carry out the methods described herein.

BRIEF DESCRIPTION OF THE DRAWINGS

Reference will now be made, by way of example, to the accompanying drawings which show example embodiments of the present application, and in which.

Similar reference numerals may have been used in different figures to denote similar components.

DESCRIPTION OF EXAMPLE EMBODIMENTS

The systems and methods described herein may be useful in the field of neurosurgery, including oncological care, neurodegenerative disease, stroke, brain trauma and orthopedic surgery. Persons of skill will appreciate the ability to extend these concepts to other conditions or fields of medicine. It should be noted that while the present disclosure describes examples in the context of neurosurgery, the present disclosure may be applicable to other procedures that may benefit from feedback to guide selection, modification and/or fabrication of artificial bone implants, including where such selection, modification and/or fabrication takes place intra-operatively or nearly real-time during (e.g., in parallel with) surgery, as well as where such selection, modification and/or fabrication takes place pre-operatively.

Various example apparatuses or processes will be described below. No example embodiment described below limits any claimed embodiment and any claimed embodiments may cover processes or apparatuses that differ from those examples described below. The claimed embodiments are not limited to apparatuses or processes having all of the features of any one apparatus or process described below or to features common to multiple or all of the apparatuses or processes described below. It is possible that an apparatus or process described below is not an embodiment of any claimed embodiment.

Furthermore, numerous specific details are set forth in order to provide a thorough understanding of the disclosure. However, it will be understood by those of ordinary skill in the art that the embodiments described herein may be practiced without these specific details. In other instances, well-known methods, procedures and components have not been described in detail so as not to obscure the embodiments described herein.

A neurosurgical procedure often is preceded with pre-operative planning of the procedure. Pre-operative planning may be used alone or combined with intra-operative guidance and navigation systems and methods, for example wherein information collected during the surgical procedure is used to guide the next surgical steps, or measure predicted patient outcome. Examples of systems and methods for planning a neurosurgical procedure are described in PCT application no. PCT/CA2014/050272, titled "PLANNING, NAVIGATION AND SIMULATION SYSTEMS AND METHODS FOR MINIMALLY INVASIVE THERAPY", which claims priority from U.S. provisional patent application Nos. 61/800,155 and 61/924,993. The entireties of all these disclosures are incorporated herein by reference.

Figure 8:
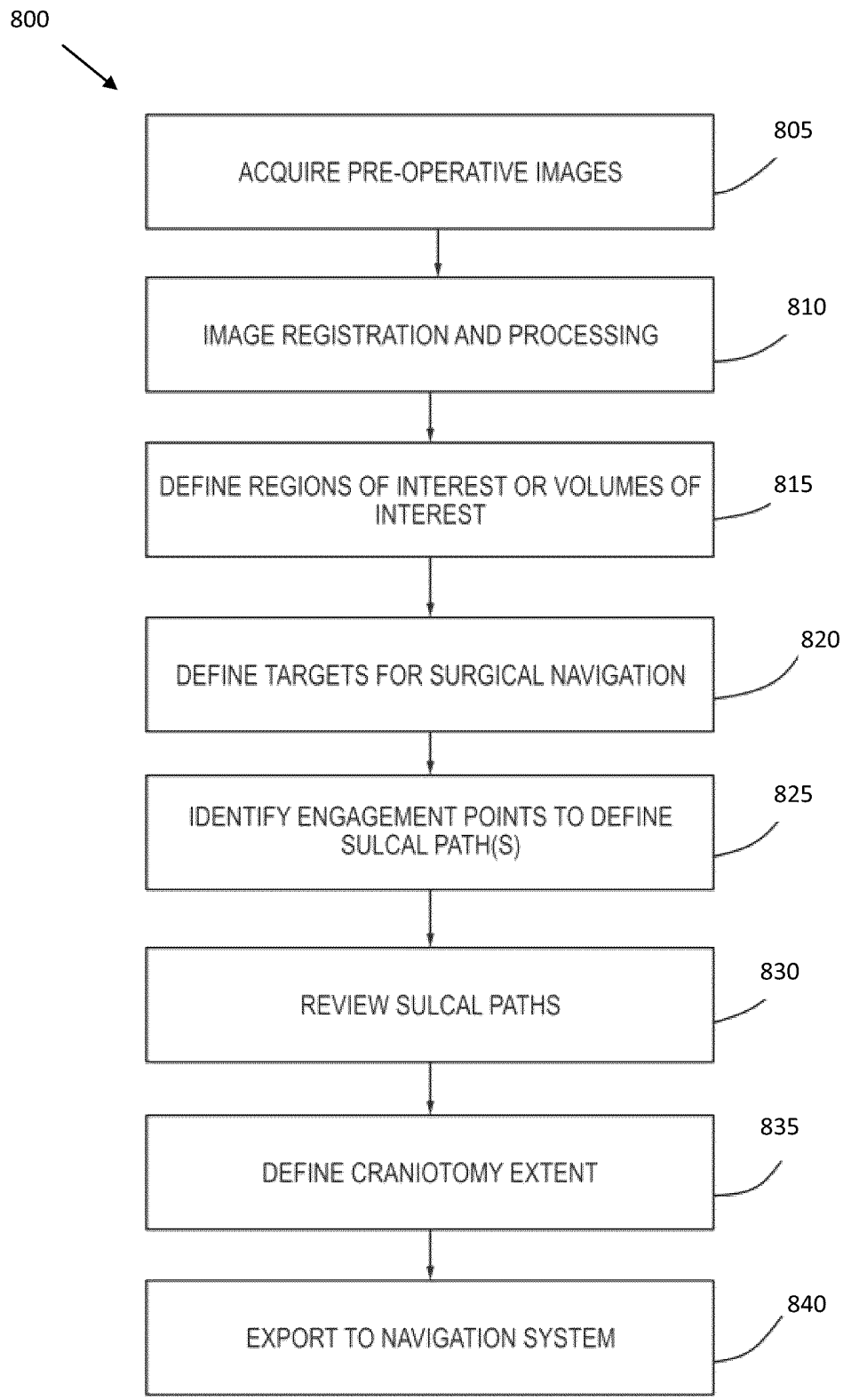
FIG. 8 is a flowchart illustrating an example method for planning a neurosurgical procedure.

FIG. 8 is a flowchart illustrating an example method 800 for planning a neurosurgical procedure. The example method 800 may be performed by a planning system, which may be implemented using a control and processing unit 500 as described in FIG. 5 below, executing suitable planning software.

At 805, pre-operative image data of the patient are acquired. The image data may be first imported into the planning software from a database or a server, such as a picture archiving and communication system (PACS) server. The pre-operative image data (i.e., those images obtained prior to initiation of the surgical procedure) may be obtained using at least one, or any combination of, magnetic resonance imaging (MRI), computer tomography (CT), positron emission tomography (PET) or similar modalities which have the necessary tissue penetration to image the desirable parts of the brain prior to invasive procedures being initiated. The image data may include images of fiducial markers or other reference points for orienting the image data in space. The pre-operative image data may be three-dimensional (3D).

In some examples, the imaging data may include more than one imaging modality. In this situation, at 810, the image data from the different modalities may be co-registered with each other to give combined information. For example, MR data may be obtained under conditions suitable to acquire both diffusion data and to obtain MR data useful to generate a 3D sulcal surface map. The pre-operative MR image data from which the diffusion images are obtained may be co-registered with each other as is also done with the MR image data used to obtain the 3D sulcal surface since each MR imaging modality would have its own orientation, geometric scaling and distortions.

At 815, one or more specific regions of interest (ROIs) may be defined. For example, through the use of a suitable user interface provided by the planning software (e.g., as displayed on a screen of the planning system), the ROI(s) can be defined by a user (e.g., a surgeon) on one or more displayed images, such as 2D image layers displayed by the user interface. This user input may be provided using interactive tools provided by the user interface, such as a point-and-click tool or a click-and-drag brush tool. After the ROI(s) have been defined in the 2D image(s), corresponding defined volumes of interest (VOIs) can be calculated by interpolating between such defined ROI(s). Additionally or alternatively, a specific point in an image layer may be selected by the user to provide an initial estimate of a ROI and a software algorithm may be employed to extrapolate the specific point to define a ROI in the 2D image layer. Various techniques may be suitable for defining the ROI(s) and/or VOI(s).

A defined ROI or VOI may represent a surgical target, such as a lesion or a region to be resected. The VOI may provide an estimate of the mass of the lesion, tumor or other region that must be resected, which may be useful to a surgeon during surgery. In some examples, a ROI or VOI may represent a region to be avoided, and planning may be performed to preserve such a region while still being able to access a target pathology region (e.g. a lesion, tumor, or blood clot, among others). Identification of region(s) to be avoided may be used to score or otherwise evaluate the suitability of proposed surgical paths, after such paths have been defined, as discussed further below.

At 820, one or more targets may be identified in the images. A target may correspond to a 3D location within the brain that must be accessed to resect the tumor or lesion. The target(s) may be defined by the user, for example using software tools (e.g., point-and-click markers) provided by the user interface.

At 825, an entry point, which is also known as an engagement point, is identified. It is noted that this entry point refers to the entry point of the leading section of the surgical port tool into the dura of the brain. There may be another entry point of the surgical port into the white brain matter. The first entry point mentioned above may be identified by providing an image (e.g., on the user interface displayed on a screen of the planning system) of the patient's brain, including sulci, with an overlay of a virtual access tool, such as a port tool, biopsy needle, or catheter, for example. In some examples, the virtual access tool may be presented in such visualizations in a manner that avoids obscuring the brain (e.g., by showing a translucent model of the tool).

The target and the engagement point(s) may be used as navigational benchmarks to define a sulcal path. For example, the planning system may be configured to define a piecewise linear sulcal path that includes the engagement and target points as the two extreme beginning and end points respectively in the surgical path and additional spatial locations between the two extreme points. These additional spatial location points may be inserted to define a piecewise linear path when turns are observed in the sulci. The piecewise linear path that closely follows the turns in the sulci may help to preserve the regions of the brain that are contacted by the surgical tool where such surgical tool is of low profile, and/or flexible or articulated. Hence, an articulated or flexible port may utilize such piecewise linear path to further reduce trauma to the brain. There may be more than one sulcal path defined (e.g., different sulcal paths may be calculated by the planning software according to different algorithms and/or to access optional targets).

At 830, the sulcal path(s) may be reviewed using a metric or score. The metric or score may be calculated for a specific sulcal path to indicate the extent of brain tracts that are intersected by the virtual port. Such a score may be used as a measure of trauma expected to be introduced by the port when using the planned sulcal path.

At 835, the craniotomy extent may be defined. This may include evaluating alternative location(s) and geometry(ies) for craniotomy by modeling surgical tools and assessing the range of motion available for each tool when the tool's motion is constrained by the dimensions and location of the craniotomy. A final scorecard may be created to present all the metrics from each of the preceding stages and a metric may be calculated to represent goodness of fit for each of the defined sulcal path(s). The goodness of fit for a sulcal path (also known as sulcal correspondence percentage) may be defined as the ratio of the planned trajectory and the sum of total length of the described sulcal path plus the Euclidian distance from the end of the path to the target. This ratio may be expressed as a percentage. This metric may indicate the correspondence between the linear trajectory and the chosen sulcal path. One hundred percent indicates a perfect match or a linear path.

In some examples, defining sulcal path(s), reviewing sulcal path(s) and defining craniotomy extent may be an iterative process, which may be repeated until a desired sulcal path with acceptable metric or score is achieved.

The user may be prompted to select and/or confirm a final accepted sulcal path. Prior to final confirmation, the user may be provided an opportunity to review the surgical plan, including location and size of the skull opening, identification of target(s) and/or identification of region(s) to avoid. The user may also be provided an opportunity to select implants (e.g., artificial bone and/or bone fasteners) that will be used in the procedure. The selection of implants may be guided by feedback provided by the planning system, as discussed further below.

At 840, the established surgical plan may be stored (e.g., locally or remotely) and/or exported to a navigation system that can typically receive such data and store and/or co-register (if appropriate) such a plan or surgical path for the surgeon to use during the surgical procedure.

In some examples, the planning system may allow the surgeon to visualize the entire procedure and compare alternative surgical plans by automatically playing back the planned surgical steps as a video. This may aid the surgeon in visualizing the entire procedure and may also serve as a confirmatory step and/or as a training step for the surgeon.

After the planning stage has been completed (e.g., via the example method 800) and the procedure has started, intra-operative image data may be acquired, for example as discussed further below. Intra-operative image data may use the same or different imaging modalities as the pre-operative image data. For example, intra-operative image data may be acquired using other imaging modalities that would not be suitable for acquiring pre-operative image data (e.g., 3D scanning, OCT, PS-OCT, and/or ultrasound, among others). These other imaging modalities may be used in addition to the above mentioned MRI, CT and PET modalities.

Figure 9:
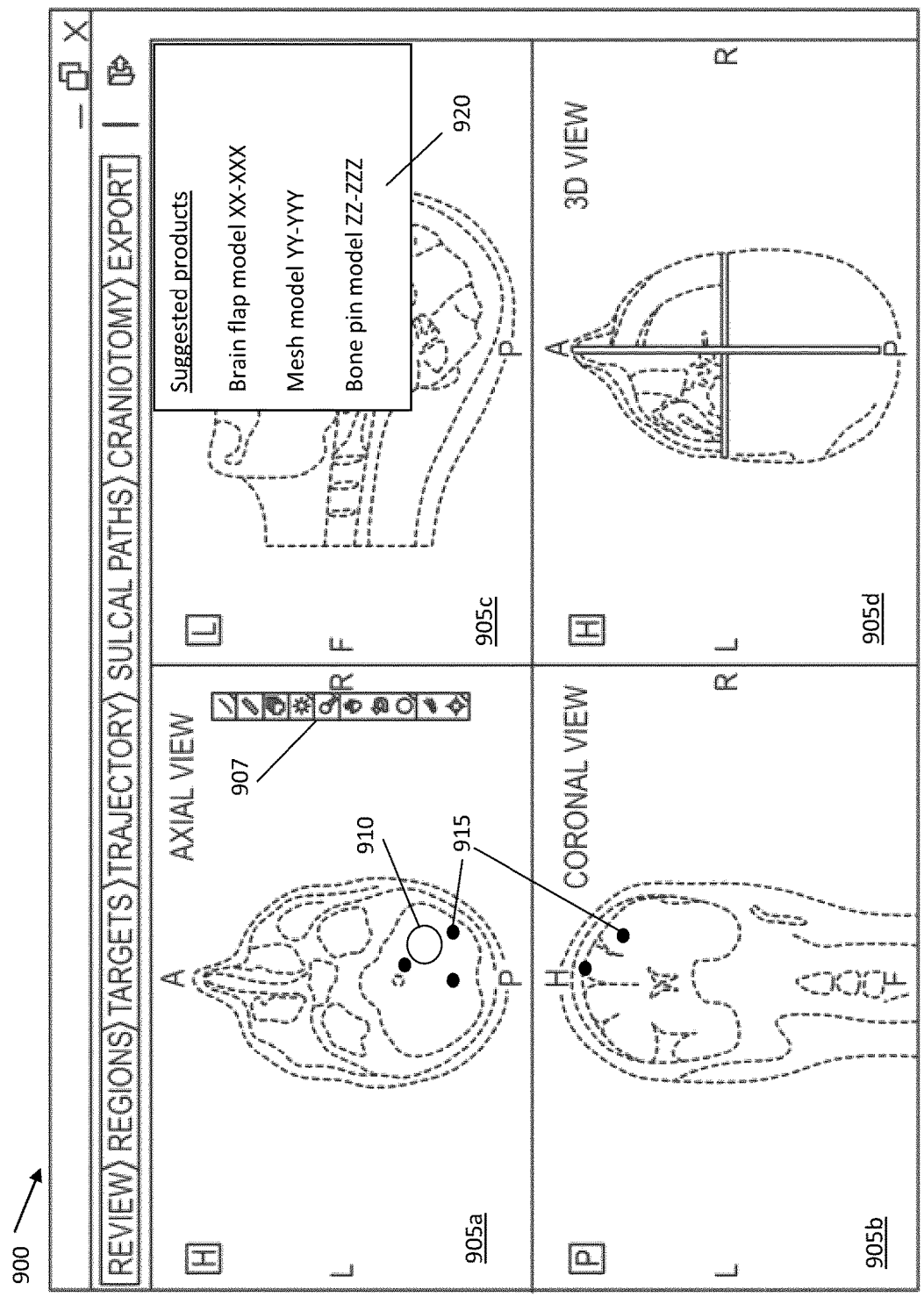
FIG. 9 shows an example output and user interface for planning a neurosurgical procedure.

During the example method 800, the planning system may provide a user interface and output on a display of the planning system. FIG. 9 shows an example user interface 900 that may be provided at a stage of the example method 800. The user interface 900 may be provided to the user at or near the end of the planning phase, for example prior to exporting to the navigation system. The user interface 900 may display different views of the 3D image data, including an axial 2D view 905*a*, a coronal 2D view 905*b*, a sagittal 2D view 905*c*, and a 3D view 905*d*. The user interface 900 may include a toolbar 907 providing user selectable tools for navigating and interacting with the user interface 900.

The views 905*a*, 905*b*, 905*c*, 905*d* may be registered with each other such that navigation and/or interaction with one view are reflected in the other views. For example, indicators of a bone opening 910 and bone fastener locations 915 may be shown in all views 905*a*, 905*b*, 905*c*, 905*d*, and user interaction with such indicators (e.g., manual repositioning of a fastener location 915) in one view may be similarly shown in other views. Further details of the example user interface 900 will be discussed with reference to FIG. 10 below.

Figure 10:
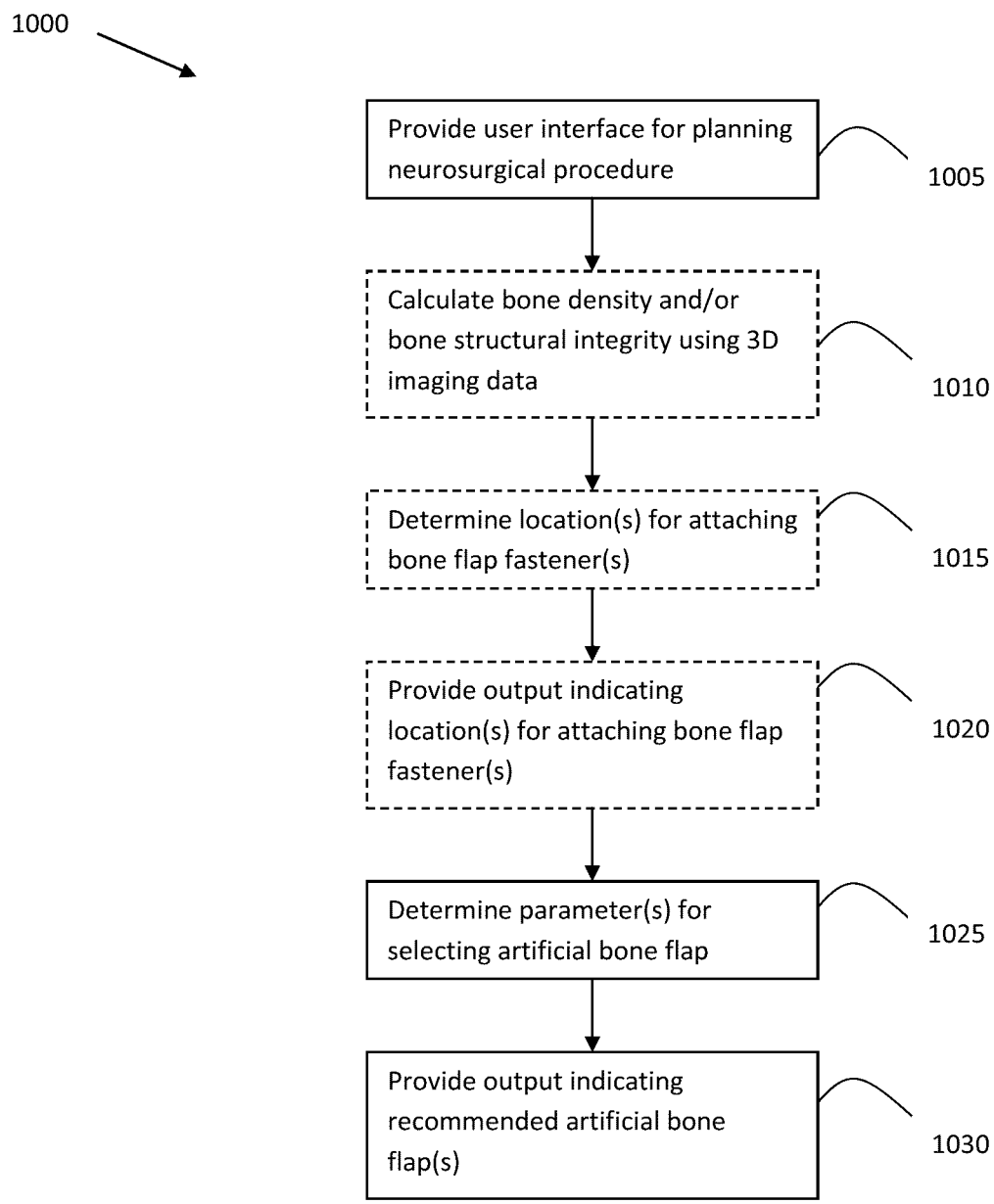
FIG. 10 is a flowchart illustrating an example method for providing feedback for selection of an artificial bone flap.

FIG. 10 shows a flowchart illustrating an example method 1000 for providing information for selection of an artificial bone flap. Although the present disclosure uses the term "artificial bone flap", it should be understood that this term is intended to encompass various implants designed to close a bone opening, including bone covers, bone meshes, and other such implants that may be referred to using other terms. It should also be understood that the implant may be made of any suitable biocompatible material, and may be fabricated using any suitable method including conventional casting and machining methods or using additive technologies such as 3D printing, for example. In some examples, fabrication of the implant may be performed just prior to the surgical procedure.

The method 1000 may take place as part of the planning method 800, for example prior to exporting the plan to a navigation system. In this example, the method 1000 may take place after the ROI(s), entry point, target point and sulcal path(s) have all been defined. The method 1000 may take place prior to the user providing final confirmation of the surgical plan. In other examples, the method 1000 may take place elsewhere in the sequence of planning steps. The example method 1000, in some cases when provided with the method 800, may provide sufficient information for the planning and execution of the surgical procedure. The example method 1000 may provide sufficient design information for just-in-time fabrication of an appropriate surgical implant.

At 1005, a user interface is provided for planning a neurosurgical procedure. This user interface may be provided by the planning system as part of the planning method 800. After the ROI(s), entry point, target point and sulcal path(s) have been defined (e.g., as described in the example method 800 above), these features may be displayed as indicators or colored overlays in 2D and/or 3D views of the patient in the user interface.

The entry point may have been defined as an opening in the patient's skull, with a defined boundary of the bone opening. The boundary of the bone opening may be automatically defined as part of the planning described above (e.g., automatically calculated based on the location of the target and entry point, and/or the expected size of the access port) and/or may be manually set or adjusted by the user. The planning software may receive user input that defines the boundary of the planned bone opening. For example, the boundary of the bone opening may be defined using a set of manually inputted points or a manually inputted trace in the 3D image.

Although FIG. 9 shows a circular indicator 910 for the bone opening, the bone opening may have other geometries and may be irregular in shape, which would be reflected in the geometry of the indicator 910.

In a neurosurgical procedure that includes closure of the bone opening, there may be a range of available (e.g., pre-made or off-the-shelf) artificial bone flaps that may be used for bone closure. It may be difficult and/or time consuming for a surgeon to select an appropriate artificial bone flap from all available bone flaps. For example, without guidance, a surgeon may resort to intra-operative trial-and-error to identify an appropriate artificial bone flap by testing different artificial bone flaps against an opening in a patient's skull. It may be useful for the planning system to provide feedback identifying or recommending one or more artificial bone flaps as being suitable for closing a given bone opening. This identification of one or more recommended parts may be performed automatically by the planning system using a suitable software algorithm, which may use features such as surface area and/or curvature of the skull opening to search through and identify suitable candidate(s) from a library or database of existing pre-fabricated or pre-designed parts. Such a library or database may be provided by a parts ordering site or parts fulfillment system, which may be external to the planning system. In some examples, the search through the database may be carried out using any suitable feature-based search algorithm, such as those used in the pattern recognition field, including a nearest neighbor algorithm or a maximum likelihood algorithm.

In some examples, it may be further useful for the planning system to help identify suitable available (e.g., off-the-shelf) bone fasteners (e.g., bone screw, bone staple and/or bone adhesive, among others) for fastening the artificial bone flap, as well as suitable locations for placing the bone fasteners. It should be understood that the identification of recommended artificial bone flaps may be dependent on the selection of which bone fastener to use, and vice versa.

Pre-operative image data, including pre-operative 3D imaging data (e.g., CT and/or MRI data) may be used to determine the 3D dimensions of the planned bone opening. The 3D dimensions of the opening may be determined by determining the dimensions (e.g., thickness, curvature and diameter) of the patient's skull within the defined boundary of the bone opening.

At 1010, bone density and/or bone structural integrity may be calculated for bone in the vicinity of the planned bone opening. The bone density and/or bone structural integrity may be calculated using pre-operative 3D imaging data. For example, CT and/or MRI image data may provide information about the thickness and density of the patient's skull in the vicinity of the planned bone opening. Such information may be obtained from image data using a suitable estimation method, such as those found in the medical imaging field. Examples of such methodology is provided in, for example, "Estimation of mechanical properties of cortical bone by computed tomography," Susan M Snyder and Erich Schneider, Journal of Orthopedic Research, Vol 9, Issue 3, May 1991. Other information (e.g., patient age and patient sex), which may be provided as part of the planning process, may be used to calculate the bone density and/or bone structural integrity as may be done in the medical imaging field. Examples of such other factors are described in, for example, "Environmental and genetic factors affecting bone mass similarity of bone density among members of healthy families," Pierre Jouanny et. Al., Vol 38, Issue 1, January 1995, Arthritis & Rheumatism. Such calculations using pre-operative image data may involve extensive modeling, calculations, finite element analysis etc. These calculations may involve modeling of the bone structure as composed of many interconnected structures that are small enough to apply a linear model for their respective mechanical properties. Several millions of such small structures may then be combined to arrive at an estimate of the mechanical property of the entire structure. This is an approach that may be adopted in finite element analysis. It should be noted that such complex and numerous computations are not feasible to be completed by a human in any practical sense, and requires the power of a computer to iteratively estimate the overall property.

Calculation of the bone density and/or bone structural integrity in the vicinity of the bone opening may be used to determine which bone fasteners would be appropriate and where the bone fasteners should be placed, as discussed further below. For example, if the bone in the vicinity of the bone opening is found to be thin or low density, the planning software may determine that a bone adhesive is more appropriate than a bone screw for fastening the artificial bone flap. Further, the planning software may determine that it is more appropriate to locate the bone fasteners (e.g., bone adhesives) farther away from the bone opening to avoid weakening the bone in the vicinity of the bone opening.

At 1015, one or more locations suitable for attaching one or more bone flap fasteners may be determined. This determination may be carried out based on the bone density and/or bone structural integrity calculated at 1010. The planning software may have a stored set of rules or guidelines that guide bone fastener location determination. For example, there may be a rule that the bone fastener must be located at least 1 cm away from the boundary of the bone opening. There may be another rule that the bone fastener must be located where the bone thickness or bone density is greater than a defined threshold. Such rules and guidelines may be preset in the planning software (e.g., as a hospital policy or preset by the surgeon). In some examples, one or more suitable areas for attachment of bone fastener(s) may be presented visually as a pseudo-color map on a 3D surface image of the patient's skull. This may aid the user in visualizing suitable location(s) for bone fastener(s) and may help the user to understand alternatives for decision making during the surgical procedure.

At 1020, output indicating the recommended location(s) for attaching bone fastener(s) may be provided. For example, the user interface 900 may display bone fastener location indicator(s) 915 overlaid on the 2D and/or 3D views 905a, 905b, 905c, 905d. These location indicator(s) 915 may be manually adjustable by the user, for example using point-and-click tools provided by the toolbar 907. In some examples, where manual adjustment of a location indicator results in a location that would contravene a preset rule or guideline (e.g., the user manually moves a location indicator to an area of low bone density), the user may be provided with feedback such as a warning dialog.

At 1025, one or more parameters for selecting an artificial bone flap may be determined. The parameter(s) may include, for example, the 3D dimensions of the bone opening, which may guide the recommended dimensions for the artificial bone flap (e.g., must have a diameter greater than that of the bone opening and/or must have a curvature similar to that of the bone opening) and/or suitable material(s) for the artificial bone flap (e.g., must be made of material(s) having a minimum amount of flexibility). In examples where recommended location(s) for placing bone fastener(s) have been determined (e.g., in 1015 above), the parameter(s) may include requiring the artificial bone flap to be large enough to be secured at the recommended bone fastener location(s). In examples where bone density and/or bone structural integrity have been calculated, these may also be the basis for parameter(s) for selecting the artificial bone flap (e.g., the artificial bone flap should have a density similar to the bone density in the vicinity of the planned bone opening). Other parameters that may be used for selecting the artificial bone flap may include bone thickness in the vicinity of the bone opening, or a patient characteristic (e.g., patient age or patient sex), among others.

One or more recommended artificial bone flaps may then be identified based on the parameter(s). The recommended artificial bone flap(s) may be identified from a database (e.g., stored locally at the planning system or accessed remotely from an ordering site or fulfillment system) of all available artificial bone flaps (e.g., a database of the inventory available in a hospital). For example, only the artificial bone flaps that match the recommended dimensions (e.g., within a range of +/−1 cm) may be recommended.

In some examples, one or more recommended bone fasteners may also be identified by the planning system. The bone fastener(s) may be identified based on compatibility with the recommended artificial bone flap(s). In some examples, recommended bone fastener(s) may be identified after the user has selected an artificial bone flap. In examples where bone density and/or bone structural integrity have been calculated, identification of recommended bone fastener(s) may also be based on determination of what is suitable given the bone density and/or bone structural integrity in the vicinity of the planned bone opening.

At 1030, output indicating the recommended artificial bone flap(s) may be provided to the user. For example, a list of recommended artificial bone flap(s), including model number, may be presented in a list 920 on the user interface 900. Although FIG. 9 shows the list 920 as a drop-down list, in some examples the list 920 may be displayed to the side of the views 905a, 905b, 905c, 905d so as to avoid obscuring any images. The entries in the list 920 may include the recommended artificial bone flap(s) as well as recommended bone flap fastener(s). The user may select one or more entries from the list 920 to be included in the final surgical plan. Alternatively, the user may simply accept all recommended entries.

In some examples, the method 1000 may omit steps 1010 and/or 1015, in which case the method 1000 may also omit step 1020 and may not provide output indicating recommended bone fasteners and/or locations for attaching the bone fasteners.

In some examples, the method 1000 may recommend, in addition to an artificial bone flap that best matches the 3D dimensions of the bone opening, additional artificial bone flaps that are larger and smaller (e.g., +/−10% in dimension) than the best match. This may be useful in case the actual intra-operative bone opening is larger or smaller than planned.

In some examples, the method 1000 may further provide output to guide modification of a selected artificial bone flap. For example, a surgeon may manually manipulate a bone mesh to shape the mesh to conform to the curvature of a patient's skull. By providing guidance to the surgeon, the method 1000 may reduce or eliminate the repeated trial-and-error manipulation of the mesh.

After an artificial bone flap has been selected (e.g., an entry is selected from the list 920 provided in the user interface 900) the planning software may obtain the 3D dimensions of the selected artificial bone flap (e.g., obtaining the known dimensions from a database) and compare these 3D dimensions to the 3D dimensions of the bone opening. The difference between the 3D dimensions of the selected artificial bone flap and the 3D dimensions of the bone opening may be used to provide guidance for modifying the artificial bone flap. For example, if it is determined that the curvature of the selected artificial bone flap is less than that of the bone opening, the user may be provided with output (e.g., in the form of text and/or graphical display on the user interface 900) to manually shape the artificial bone flap to more closely match the curvature of the bone opening.

In some examples, the guidance for manually shaping the artificial bone flap may be based on intra-operative image data, as discussed below.

Once one or more artificial bone flaps (and optionally bone fastener(s)) have been selected, the selection(s) may be outputted from the planning system to a part ordering site or fulfillment system (which may be external to the planning system) to order the part(s).

In some examples, instead of selecting an available artificial bone flap, the user may choose instead to have a custom-made artificial bone flap fabricated based on the determined 3D dimensions of the bone opening. In such a case, the 3D dimensions of the bone opening may be exported (e.g., as a digital model) to a 3D fabrication system (which may be part of a bone flap ordering system), as discussed further below.

Although the example method 1000 has been described with respect to closing of a planned bone opening, the method 1000 may be adapted for closing of an already existing bone opening. This may be done by calculating the 3D dimensions of the existing bone opening using a comparison of 3D image data before and after creation of the bone opening, or by extrapolating the curvature of the skull over the bone opening, for example. An example of such extrapolation is described with respect to FIG. 7B at 778 below.

Figure 7A:
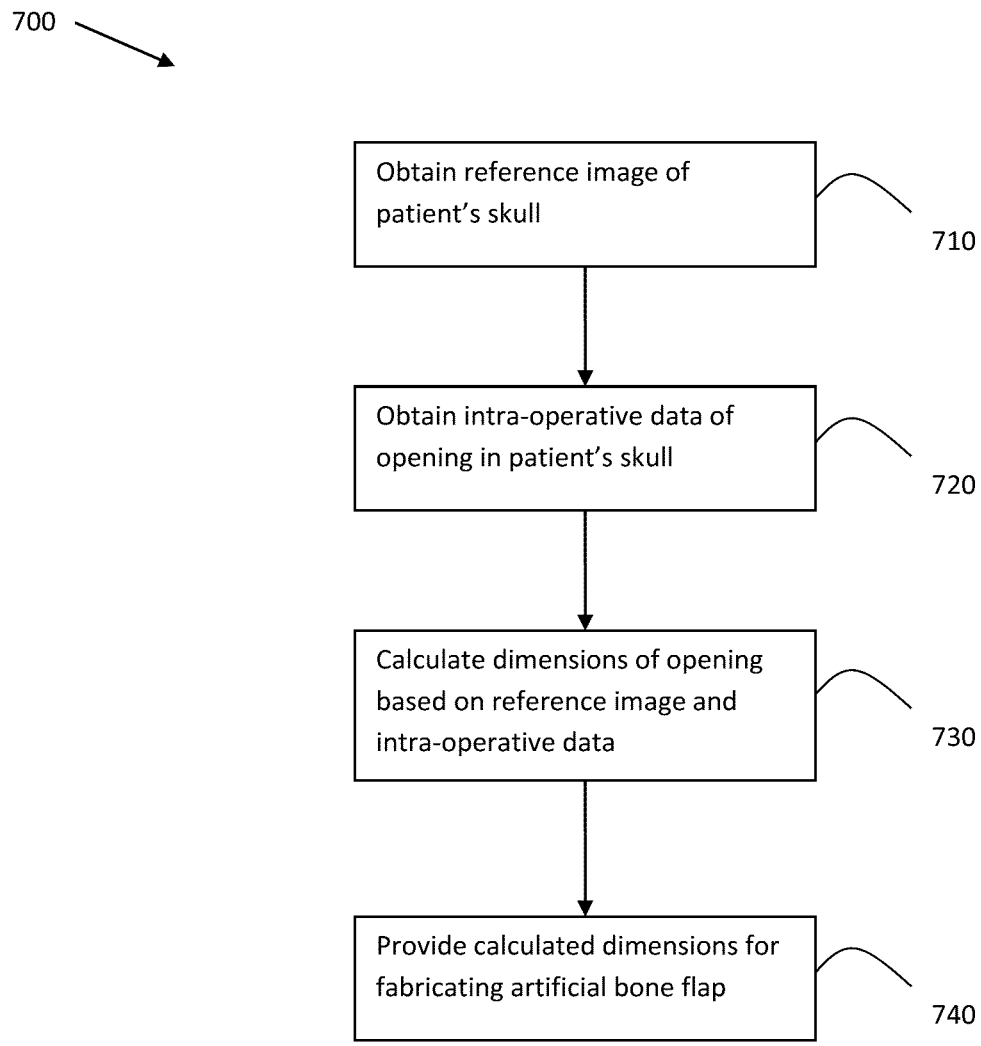
FIGS. 7A and 7B are flowcharts illustrating an example method for determining dimensions for fabricating and artificial bone flap.
Figure 7B:
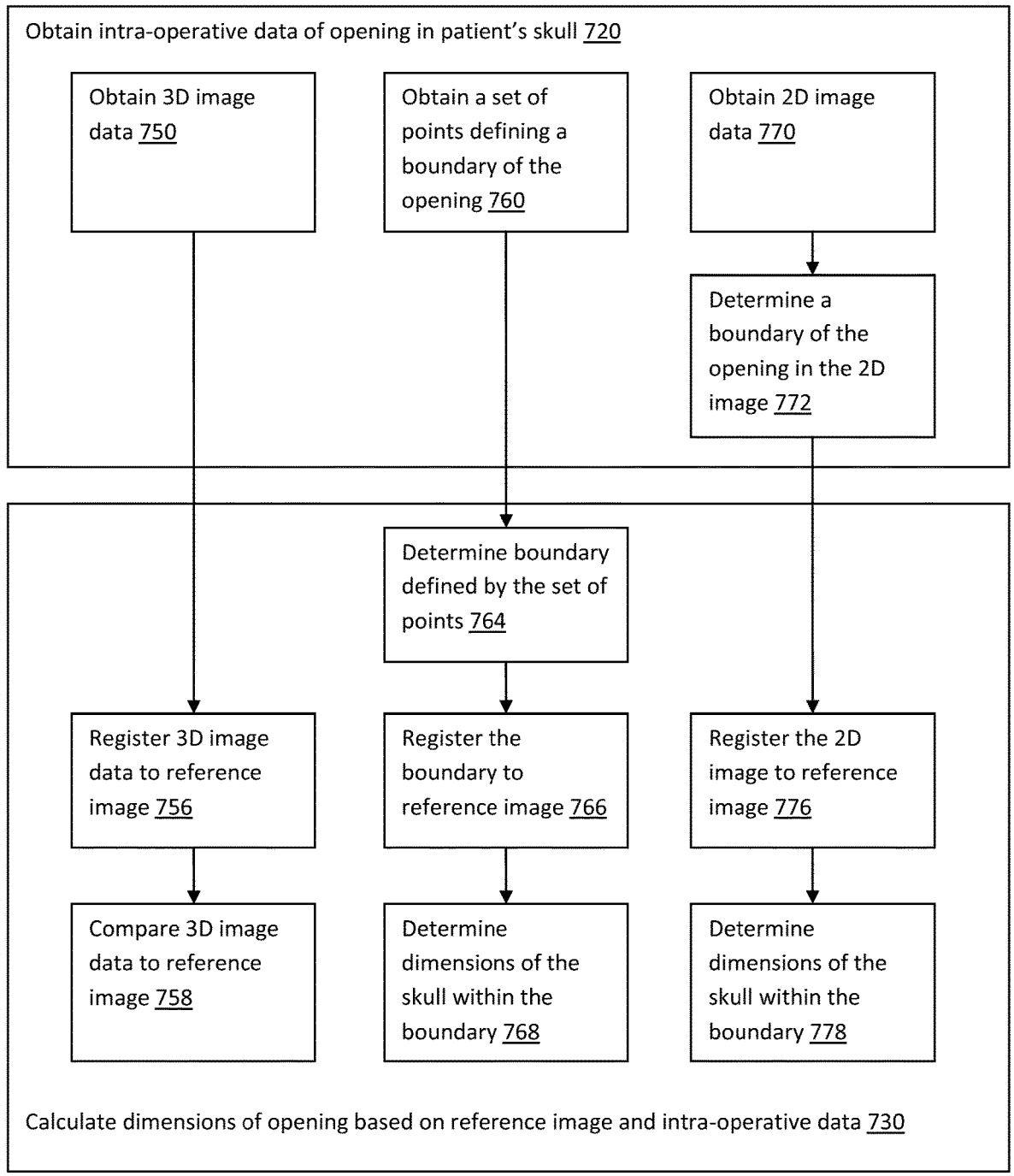

Although FIGS. 7A and 7B illustrate intra-operative steps, it should be understood that certain aspects, such as determining 3D dimensions of an existing bone opening (e.g., at 758, 768 and 778), calculating dimensions for fabricating the artificial bone flap, and fabrication of an artificial bone flap (e.g., at 740), may be implemented pre-operatively as well.

The finalized surgical plan, which may include a selection of artificial bone flap(s) and/or bone fastener(s), may be exported for use during the surgical procedure.

Figure 1:
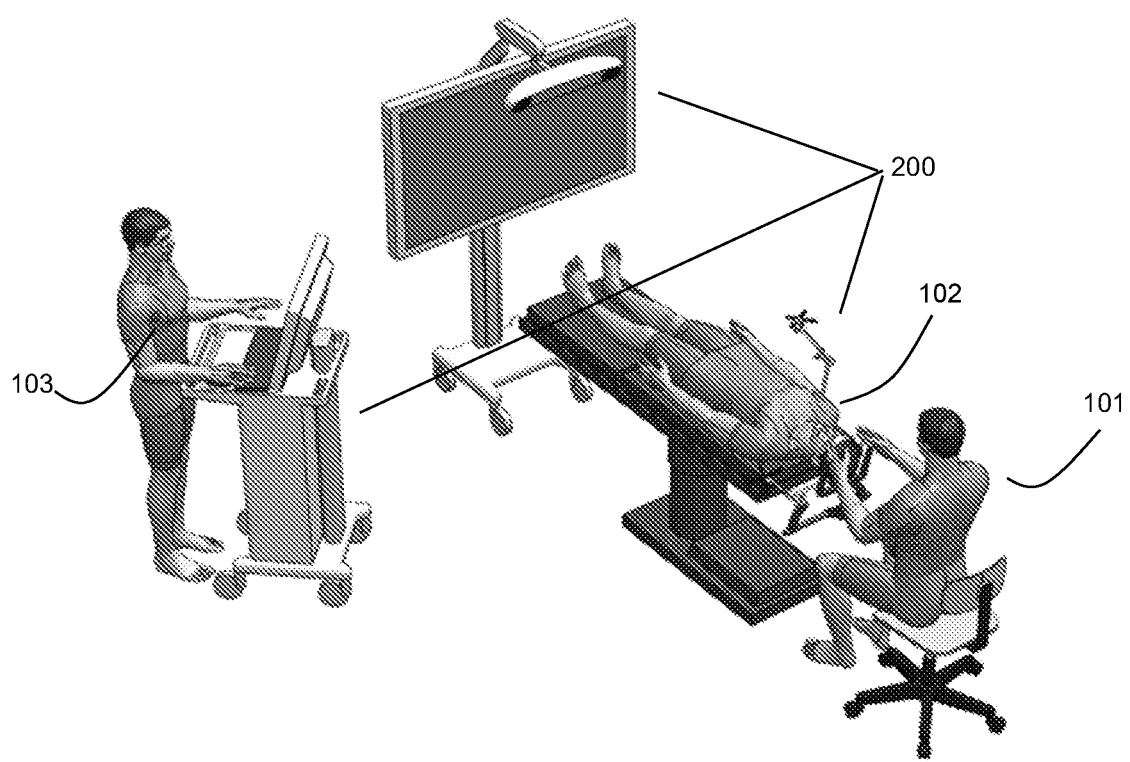
FIG. 1 shows an example navigation system to support minimally invasive access port-based surgery.

FIG. 1 illustrates a perspective view of an example minimally invasive port-based surgical procedure. As shown in FIG. 1, a surgeon 101 may conduct a minimally invasive port-based surgery on a patient 102 in an operating room (OR) environment. A craniotomy may be performed as part of the minimally invasive surgery, to provide access to the patient's brain. A localization or navigation system 200 (described further below) may be used to assist the surgeon 101 during the procedure. Optionally, an operator 103 may be present to operate, control and provide assistance with the navigation system 200.

Figure 2A:
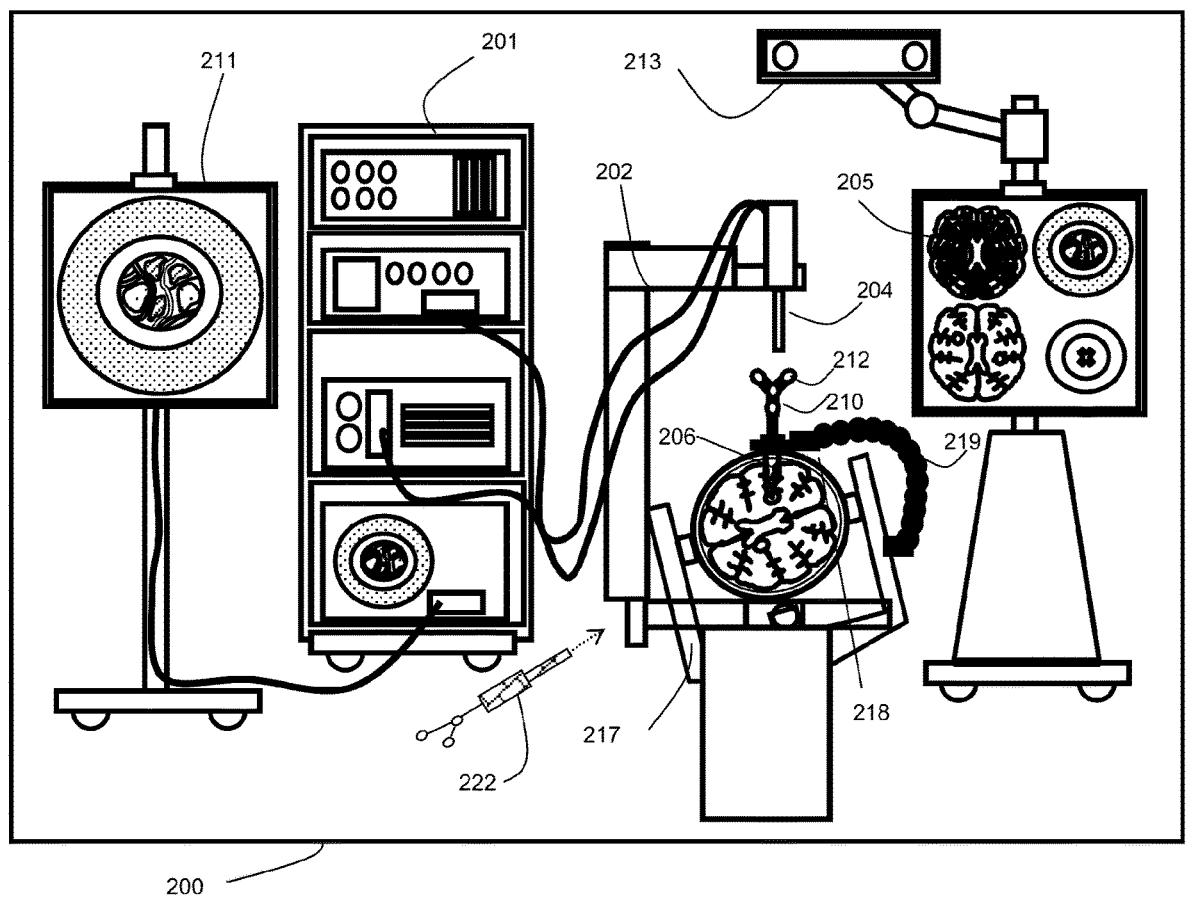
FIG. 2A is a diagram illustrating system components of an example navigation system.

FIG. 2A shows a diagram illustrating components of an example medical navigation system 200. The disclosed methods and systems for determining dimensions for fabrication of an artificial bone flap may be implemented in the context of the medical navigation system 200. The medical navigation system 200 may include one or more displays 205, 211 for displaying a video image, an equipment tower 201, and a mechanical arm 202, which may support an optical scope 204 (which may also be referred to as an external scope). One or more of the displays 205, 211 may include a touch-sensitive display for receiving touch input. The equipment tower 201 may be mounted on a frame (e.g., a rack or cart) and may contain a power supply and a computer or controller that may execute planning software, navigation software and/or other software to manage the mechanical arm 202 and tracked instruments. In some examples, the equipment tower 201 may be a single tower configuration operating with dual displays 211, 205, however other configurations may also exist (e.g., dual tower, single display, etc.). Furthermore, the equipment tower 201 may also be configured with a universal power supply (UPS) to provide for emergency power, in addition to a regular AC adapter power supply.

A portion of the patient's anatomy may be held in place by a holder. For example, as shown the patient's head and brain may be held in place by a head holder 217. An access port 206 and associated introducer 210 may be inserted into the head, to provide access to a surgical site in the head. The optical scope 204 may be attached to the mechanical arm 202, and may be used to view down the access port 206 at a sufficient magnification to allow for enhanced visibility down the access port 206. The output of the optical scope 204 may be received by one or more computers or controllers to generate a view that may be depicted on a visual display (e.g., one or more displays 205, 211).

Figure 2B:
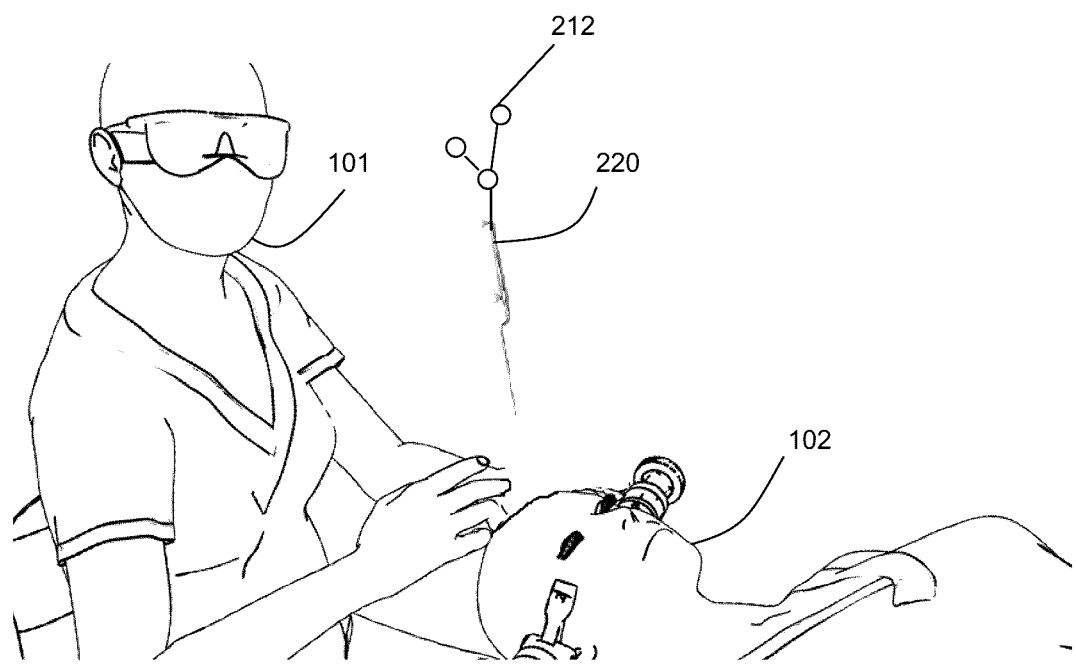
FIG. 2B is a diagram illustrating use of a tracked pointer in an example navigation system.

In some examples, the navigation system 200 may include a tracked pointer 220. The tracked pointer 220, which may include markers 212 to enable tracking by the tracking camera 213, may be used to identify points (e.g., fiducial points or points bordering a craniotomy opening, as discussed below) on a patient. FIG. 2B shows an example use of a tracked pointer 220 to identify points on a patient. As shown, an operator, typically a nurse or the surgeon 101, may use the tracked pointer 220 to identify the location of points on the patient 102, in order to register the location of selected points on the patient 102 in the navigation system 200. It should be noted that a guided robotic system with closed loop control may be used as a proxy for human interaction. Guidance to the robotic system may be provided by any combination of input sources such as image analysis, tracking of objects in the operating room using markers placed on various objects of interest, or any other suitable robotic system guidance techniques.

Reference is again made to FIG. 2A. Fiducial markers 212 may be connected to the introducer 210 for tracking by the tracking camera 213, which may provide positional information of the introducer 210 from the navigation system 200. In some examples, the fiducial markers 212 may be alternatively or additionally attached to access port 206. In some examples, the tracking camera 213 may be a 3D infrared optical tracking stereo camera similar to one made by Northern Digital Imaging (NDI). In some examples, the tracking system 213 may be an electromagnetic system (not shown), such as a field transmitter that may use one or more receiver coils located on the tool(s) to be tracked. Known profile of the electromagnetic field and known position of receiver coil(s) relative to each other may be used to infer the location of the tracked tool(s) using the induced signals and their phases in each of the receiver coils. Operation and examples of this technology is further explained in Chapter 2 of "Image-Guided Interventions Technology and Application," Peters, T.; Cleary, K., 2008, ISBN: 978-0-387-72856-7, incorporated herein by reference. Location data of the mechanical arm 202 and/or access port 206 may be determined by the tracking camera 213 by detection of the fiducial markers 212 placed on or otherwise in fixed relation (e.g., in rigid connection) to any of the mechanical arm 202, the access port 206, the introducer 210, the tracked pointer 220 and/or other pointing tools. The fiducial marker(s) 212 may be active or passive markers. The secondary display 205 may provide output of the computed data of the navigation system 200. In some examples, the output provided by the secondary display 205 may include axial, sagittal and coronal views of patient anatomy as part of a multi-view output.

The active or passive fiducial markers 212 may be placed on tools (e.g., the access port 206 and/or the optical scope 204) to be tracked, to determine the location and orientation of these tools using the tracking camera and navigation system. The markers 212 may be captured by a stereo camera of the tracking system to give identifiable points for tracking the tools. A tracked tool may be defined by a grouping of markers 212, which may define a rigid body to the tracking system. This may in turn be used to determine the position and/or orientation in 3D of a tracked tool in a virtual space. The position and orientation of the tracked tool in 3D may be tracked in six degrees of freedom (e.g., x, y, z coordinates and pitch, yaw, roll rotations), in five degrees of freedom (e.g., x, y, z, coordinate and two degrees of free rotation), but preferably tracked in at least three degrees of freedom (e.g., tracking the position of the tip of a tool in at least x, y, z coordinates). In typical use with navigation systems, at least three markers 212 are provided on a tracked tool to define the tool in virtual space, however it is known to be advantageous for four or more markers 212 to be used.

Camera images capturing the markers 212 may be logged and tracked, by, for example, a closed circuit television (CCTV) camera. The markers 212 may be selected to enable or assist in segmentation in the captured images. For example, infrared (IR)-reflecting markers and an IR light source from the direction of the camera may be used. An example of such an apparatus may be tracking devices such as the Polaris® system available from Northern Digital Inc. In some examples, the spatial position of the tracked tool and/or the actual and desired position of the mechanical arm 202 may be determined by optical detection using a camera. The optical detection may be done using an optical camera, rendering the markers 212 optically visible.

In some examples, the markers 212 (e.g., reflectospheres) may be used in combination with a suitable tracking system, to determine the spatial positioning position of the tracked tools within the operating theatre. Different tools and/or targets may be provided with respect to sets of markers 212 in different configurations. Differentiation of the different tools and/or targets and their corresponding virtual volumes may be possible based on the specification configuration and/or orientation of the different sets of markers 212 relative to one another, enabling each such tool and/or target to have a distinct individual identity within the navigation system 200. The individual identifiers may provide information to the system, such as information relating to the size and/or shape of the tool within the system. The identifier may also provide additional information such as the tool's central point or the tool's central axis, among other information. The virtual tool may also be determinable from a database of tools stored in or provided to the navigation system 200. The markers 212 may be tracked relative to a reference point or reference object in the operating room, such as the patient 102.

Various types of markers may be used. The markers 212 may all be the same type or may include a combination of two or more different types. Possible types of markers that could be used may include reflective markers, radiofrequency (RF) markers, electromagnetic (EM) markers, pulsed or un-pulsed light-emitting diode (LED) markers, glass markers, reflective adhesives, or reflective unique structures or patterns, among others. RF and EM markers may have specific signatures for the specific tools they may be attached to. Reflective adhesives, structures and patterns, glass markers, and LED markers may be detectable using optical detectors, while RF and EM markers may be detectable using antennas. Different marker types may be selected to suit different operating conditions. For example, using EM and RF markers may enable tracking of tools without requiring a line-of-sight from a tracking camera to the markers 212, and using an optical tracking system may avoid additional noise from electrical emission and detection systems.

In some examples, the markers 212 may include printed or 3D designs that may be used for detection by an auxiliary camera, such as a wide-field camera (not shown) and/or the optical scope 204. Printed markers may also be used as a calibration pattern, for example to provide distance information (e.g., 3D distance information) to an optical detector. Printed identification markers may include designs such as concentric circles with different ring spacing and/or different types of bar codes, among other designs. In some examples, in addition to or in place of using markers 212, the contours of known objects (e.g., the side of the access port 206) could be captured by and identified using optical imaging devices and the tracking system.

In some examples, the navigation system 200 may include a portable three-dimensional (3D) scanner 222. The 3D scanner 222 may be used to obtain a 3D image of a portion of the patient's anatomy, for example an opening in the skull, as described further below. The image obtained by the 3D scanner 222 may be registered in the virtual space of the navigation system 200, for example by identifying and registering fiducial markers 212 captured in the 3D image.

Minimally invasive brain surgery using an access port 206 is a method of performing surgery on brain tumors. In order to introduce an access port 206 into the brain, the introducer 210, having an atraumatic tip, may be positioned within the access port 206 and employed to position the access port 206 within the patient's brain. The introducer 210 may include fiducial markers 212 for tracking position and orientation of the introducer 210. The fiducial markers 212 may be passive (e.g., reflective spheres for use with an optical tracking system, or pick-up coils for use with an electromagnetic tracking system). The fiducial markers 212 may be detected by the tracking camera 213 and the respective positions of the tracked tool may be inferred by tracking software executed by a computer or controller in connection with the navigation system 200.

Once the access port 206 has been positioned into the brain, the associated introducer 210 may be removed to allow for access to the surgical site of interest, through the central opening of the access port 206. Tracking of the access port 206 may be provided by an access port guide or by attaching markers to the access port 206 itself.

A guide clamp 218 (or more generally a guide) for holding the access port 206 may be provided. The guide clamp 218 may allow the access port 206 to be held at a fixed position and orientation while freeing up the surgeon's hands. An articulated arm 219 may be provided to hold the guide clamp 218. The articulated arm 219 may have up to six degrees of freedom to position the guide clamp 218. The articulated arm 219 may be lockable to fix its position and orientation, once a desired position is achieved. The articulated arm 219 may be attached or attachable to a point based on the patient head holder 217, or another suitable point (e.g., on another patient support, such as on the surgical bed), to ensure that when locked in place, the guide clamp 218 does not move relative to the patient's head.

In a surgical operating room (or theatre), setup of a navigation system may be relatively complicated; there may be many pieces of equipment associated with the surgical procedure, as well as elements of the navigation system 200. Further, setup time typically increases as more equipment is added. To assist in addressing this, the navigation system 200 may include two additional wide-field cameras to enable video overlay information. One wide-field camera may be mounted on the optical scope 204, and a second wide-field camera may be mounted on the tracking camera 213. Video overlay information can then be inserted into displayed images, such as images displayed on one or more of the displays 205, 211. The overlay information may illustrate the physical space where accuracy of the 3D tracking system (which is typically part of the navigation system) is greater, may illustrate the available range of motion of the mechanical arm 202 and/or the optical scope 204, and/or may help to guide head and/or patient positioning.

The navigation system 200 may provide tools to the neurosurgeon that may help to provide more relevant information to the surgeon, and may assist in improving performance and accuracy of port-based neurosurgical operations. Although described in the present disclosure in the context of port-based neurosurgery (e.g., for removal of brain tumors and/or for treatment of intracranial hemorrhages (ICH)), the navigation system 200 may also be suitable for one or more of: brain biopsy, functional/deep-brain stimulation, catheter/shunt placement (in the brain or elsewhere), open craniotomies, and/or endonasal/skull-based/ear-nose-throat (ENT) procedures, among others. The same navigation system 200 may be used for carrying out any or all of these procedures, with or without modification as appropriate.

For example, although the present disclosure may discuss the navigation system 200 in the context of neurosurgery, the same navigation system 200 may be used to carry out a diagnostic procedure, such as brain biopsy. A brain biopsy may involve the insertion of a thin needle into a patient's brain for purposes of removing a sample of brain tissue. The brain tissue may be subsequently assessed by a pathologist to determine if it is cancerous, for example. Brain biopsy procedures may be conducted with or without a stereotactic frame. Both types of procedures may be performed using image-guidance. Frameless biopsies, in particular, may be conducted using the navigation system 200.

In some examples, the tracking camera 213 may be part of any suitable tracking system. In some examples, the tracking camera 213 (and any associated tracking system that uses the tracking camera 213) may be replaced with any suitable tracking system which may or may not use camera-based tracking techniques. For example, a tracking system that does not use the tracking camera 213, such as a radiofrequency tracking system, may be used with the navigation system 200.

Figure 3A:
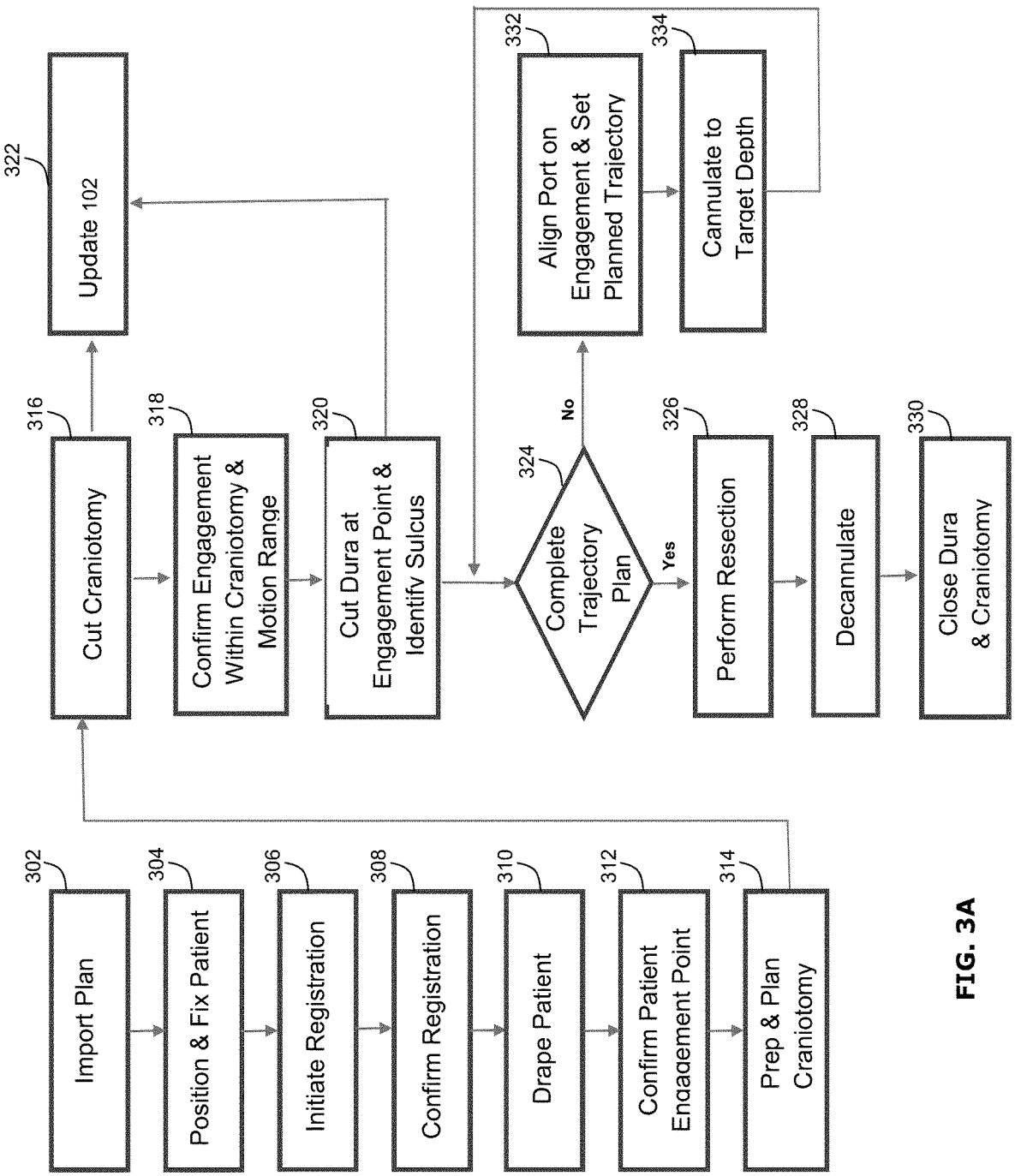
FIG. 3A is a flow chart illustrating an example method involved in a surgical procedure using the example navigation system of FIG. 2.

FIG. 3A is a flow chart illustrating an example method 300 of performing a port-based surgical procedure using a navigation system, such as the medical navigation system 200 described above. At 302, the port-based surgical plan may be imported. A detailed description of an example process to create and select a surgical plan is outlined in PCT application no. PCT/CA2014/050272, titled "PLANNING, NAVIGATION AND SIMULATION SYSTEMS AND METHODS FOR MINIMALLY INVASIVE THERAPY", previously incorporated herein by reference.

An example surgical plan may include pre-operative 3D imaging data (e.g., magnetic resonance imaging (MRI), computer tomography (CT), positron emission tomography (PET) or ultrasound data). The plan may include overlaid data, such as additional received inputs (e.g., sulci entry points, target locations, surgical outcome criteria and/or additional 3D image data information). The plan may also include a display of one or more planned trajectory paths (e.g., based on calculated score for a projected surgical path). Other surgical plans and/or methods may additionally or alternatively be used as inputs into the navigation system.

Once the plan has been imported into the navigation system at the block 302, the patient may be affixed into position (e.g., using a body holding mechanism, such as the head holder 217). The patient's head position may be also confirmed with the plan using appropriate navigation software (at 304), which in an example may be implemented by the computer or controller forming part of the equipment tower 201.

Next, registration of the patient may be initiated (at 306). The term "registration" may refer to the process of transforming different sets of data into one coordinate system. Data may include multiple photographs, data from different sensors, times, depths, or viewpoints, for example. The process of registration may be used in the context of the present disclosure for medical imaging, in which images from different imaging modalities may be co-registered. Registration may be used in order to be able to compare and/or integrate the data obtained from these different modalities.

Registration of the patient to a base reference frame may occur in various suitable ways. Example methods for registration may include:

Identification of features (natural or engineered) in the image data (e.g., MR and CT images) and indication of those same features on the actual patient using the tracked pointer 220;

Tracing a line on the curved profile of the patient's face or forehead with a pointer tool that may be tracked by the tracking camera, and matching this curved profile to the image data (e.g., 3D MR or CT volume);

Application of a tool of known geometry to the patient's face, where the tool may have targets tracked by the tracking camera; or Using a surface acquisition tool, such as the 3D scanner 222 (which may operate based on structured light), to extract a surface of the patient's face or forehead and matching the extracted surface to the 3D clinical image data (e.g., 3D MR or CT volume) that is acquired prior to or during the surgical procedure. The matching process may also be known as registration or image fusion. The process may involve, for example, aligning common features, such as anatomical structures, in images acquired using different modalities by transforming one image relative to the other. The resulting geometric transformation provides a means of correlating points in clinical images to coordinate frame of the operating room. Hence, the navigation system 200 can help a surgeon visualize the positions of physical surgical tools relative to clinical images, such as MR, CT and ultrasound.

Various registration techniques available to those skilled in the art may be suitable, and one or more of these techniques may be applied to the present disclosure. Non-limiting examples include intensity-based methods that compare intensity patterns in images via correlation metrics, as well as feature-based methods that find correspondence between image features such as points, lines, and contours, among other possible methods. Image registration methods may also be classified according to the transformation models they use to relate the target image space to the reference image space. Another classification can be made between single-modality and multi-modality methods. Single-modality methods typically register images in the same modality acquired by the same scanner or sensor type, for example, a series of MR images may be co-registered, while multi-modality registration methods are used to register images acquired by different scanner or sensor types, for example in MRI and PET. In the present disclosure, multi-modality registration methods may be used in medical imaging of the head and/or brain as images of a patient are frequently obtained from different scanners. Examples include registration of brain CT/MRI images or PET/CT images for tumor localization, registration of contrast-enhanced CT images against non-contrast-enhanced CT images, and registration of ultrasound and CT.

Figure 3B:
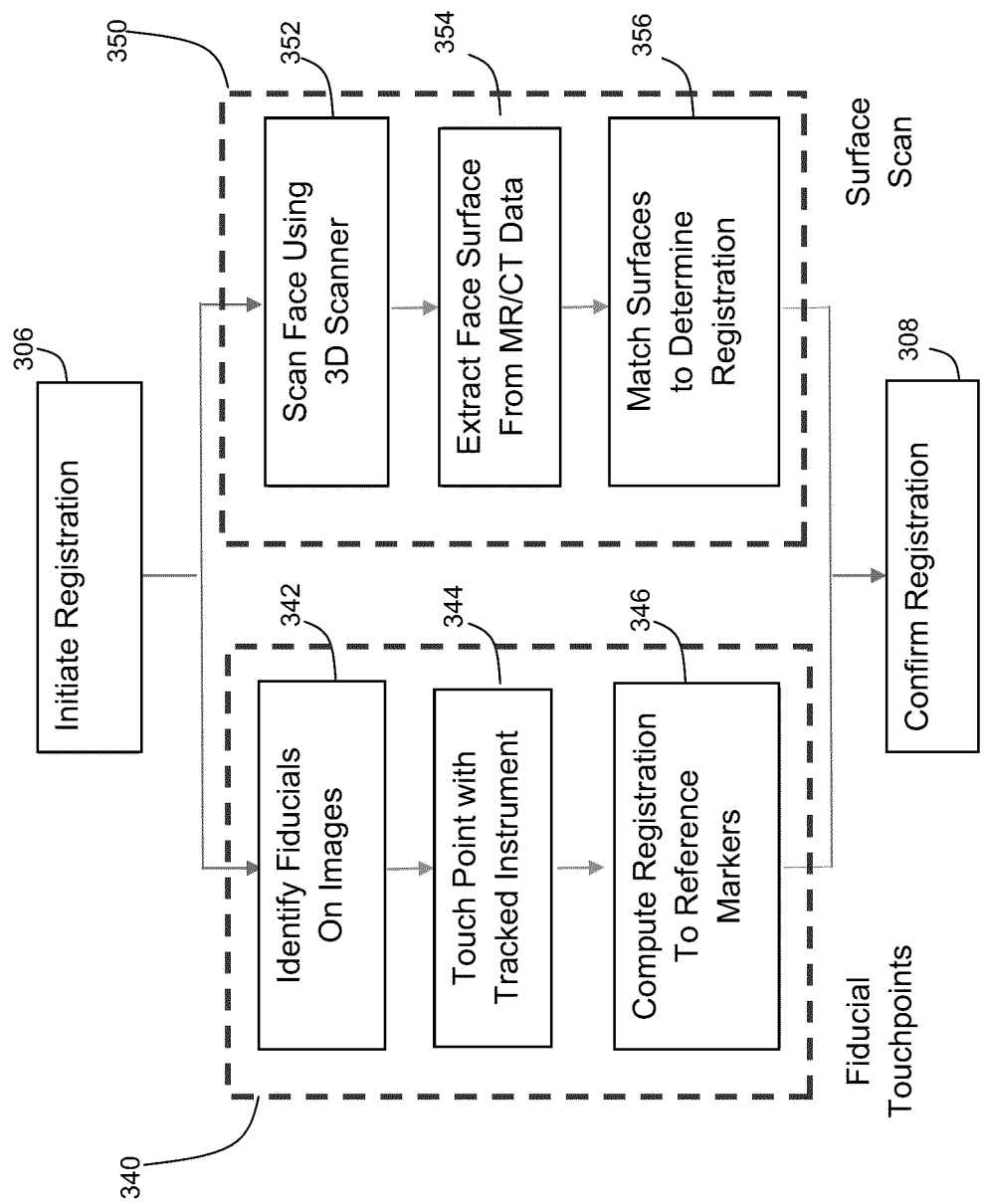
FIG. 3B is a flow chart illustrating an example method of registering a patient for a surgical procedure as outlined in FIG. 3A.

FIG. 3B shows a flow chart illustrating example methods that may be used to carry out the registration of the block 306. Block 340 illustrates an approach using fiducial touch points, while block 350 illustrates an approach using a surface scan. The block 350 is not typically used when fiducial touch points or a fiducial pointer is used.

If the use of fiducial touch points (at 340) is contemplated, the method may involve first identifying fiducial points on images (at 342), then touching the corresponding touch points on the patient with the tracked pointer 220 (at 344). Next, the navigation system may compute the registration to reference markers (at 346).

If a surface scan procedure (at 350) is used, the patient's head (e.g., face, back of head and/or skull) may be scanned using the 3D scanner 222 (at 352). Next, the corresponding surface of the patient's head may be extracted from image data (e.g., MR or CT data) (at 354). Finally, the scanned surface and the extracted surface may be matched to each other to determine registration data points (at 356).

Upon completion of either the fiducial touch points (at 340) or surface scan (at 350) procedures, the data extracted may be computed and used to confirm registration at block 308, shown in FIG. 3A.

Referring back to FIG. 3A, once registration is confirmed (at 308), the patient may be draped (at 310). Typically, draping involves covering the patient and surrounding areas with a sterile barrier to create and maintain a sterile field during the surgical procedure. Draping may be used to eliminate the passage of microorganisms (e.g., bacteria) between non-sterile and sterile areas.

Upon completion of draping (at 310), the patient engagement points may be confirmed (at 312) and then the craniotomy may be prepared and planned (at 314).

Upon completion of the preparation and planning of the craniotomy (at 314), the craniotomy may be cut and a bone flap may be removed from the skull to access the brain (at 316). In some examples, cutting the craniotomy may be assisted by a visual indication of the location, size and/or shape of the planned craniotomy (e.g., a projection of a planned outline onto the patient's skull). Registration data may be updated with the navigation system at this point (at 322).

Next, the engagement within craniotomy and the motion range may be confirmed (at 318). Next, the procedure may advance to cutting the dura at the engagement points and identifying the sulcus (at 320). Registration data may again be updated with the navigation system at this point (at 322).

In some examples, by focusing the camera's view on the surgical area of interest, update of the registration data (at 322) may be adjusted to help achieve a better match for the region of interest, while ignoring any non-uniform tissue deformation, for example, affecting areas outside of the region of interest. Additionally, by matching image overlay representations of tissue with an actual view of the tissue of interest, the particular tissue representation may be matched to the live video image, which may help to improve registration of the tissue of interest. For example, the registration may enable: matching a live video of the post craniotomy brain (with the brain exposed) with an imaged sulcal map; matching the position of exposed vessels in a live video with image segmentation of vessels; matching the position of lesion or tumor in a live video with image segmentation of the lesion and/or tumor; and/or matching a video image from endoscopy up the nasal cavity with bone rendering of bone surface on nasal cavity for endonasal alignment.

In some examples, multiple cameras can be used and overlaid with tracked instrument(s) views, which may allow multiple views of the image data and overlays to be presented at the same time. This may help to provide greater confidence in registration, or may enable easier detection of registration errors and their subsequent correction.

Thereafter, the cannulation process may be initiated. Cannulation typically involves inserting an access port into the brain, typically along a sulcus path as identified at 320, along a trajectory plan. Cannulation is typically an iterative process that may involve repeating the steps of aligning the port on engagement and setting the planned trajectory (at 332) and then cannulating to the target depth (at 334) until the complete trajectory plan is executed (at 324).

In some examples, the cannulation process may also support multi-point trajectories where a target (e.g., a tumor) may be accessed by cannulating to intermediate points, then adjusting the cannulation angle to get to the next point in a planned trajectory. This multi-point trajectory may be contrasted with straight-line trajectories where the target may be accessed by cannulating along a straight path directly towards the target. The multi-point trajectory may allow a cannulation trajectory to skirt around tissue that the surgeon may want to preserve. Navigating multi-point trajectories may be accomplished by physically reorienting (e.g., adjusting the angle of) a straight access port at different points along a planned path, or by using a flexible port, such as an access port with manipulatable bends that may be bent along the multi-point trajectory. In some examples, the skull opening created by the craniotomy at 316 may be widened by cutting out more bone during the cannulation process. Widening of the skull opening may be needed to achieve the desired cannulation angle, for example, where the original craniotomy was found to be insufficient.

Once cannulation of the access port is complete, the surgeon may perform resection (at 326) to remove part of the brain and/or tumor of interest, with or without having first removed the introducer (if used). The surgeon may then decannulate (at 328) by removing the port from the brain. Finally, the surgeon may close the dura and complete the craniotomy (at 330). Closure of the craniotomy may involve replacement of the bone flap removed at 316, or may involve closure using an artificial bone flap, which may be fabricated intra-operatively as described further below. Some aspects of FIGS. 3A and 3B may be specific to port-based surgery, such as portions of blocks 328, 320, and 334. Appropriate portions of these blocks may be skipped or suitably modified when performing non-port-based surgery.

Figure 4:
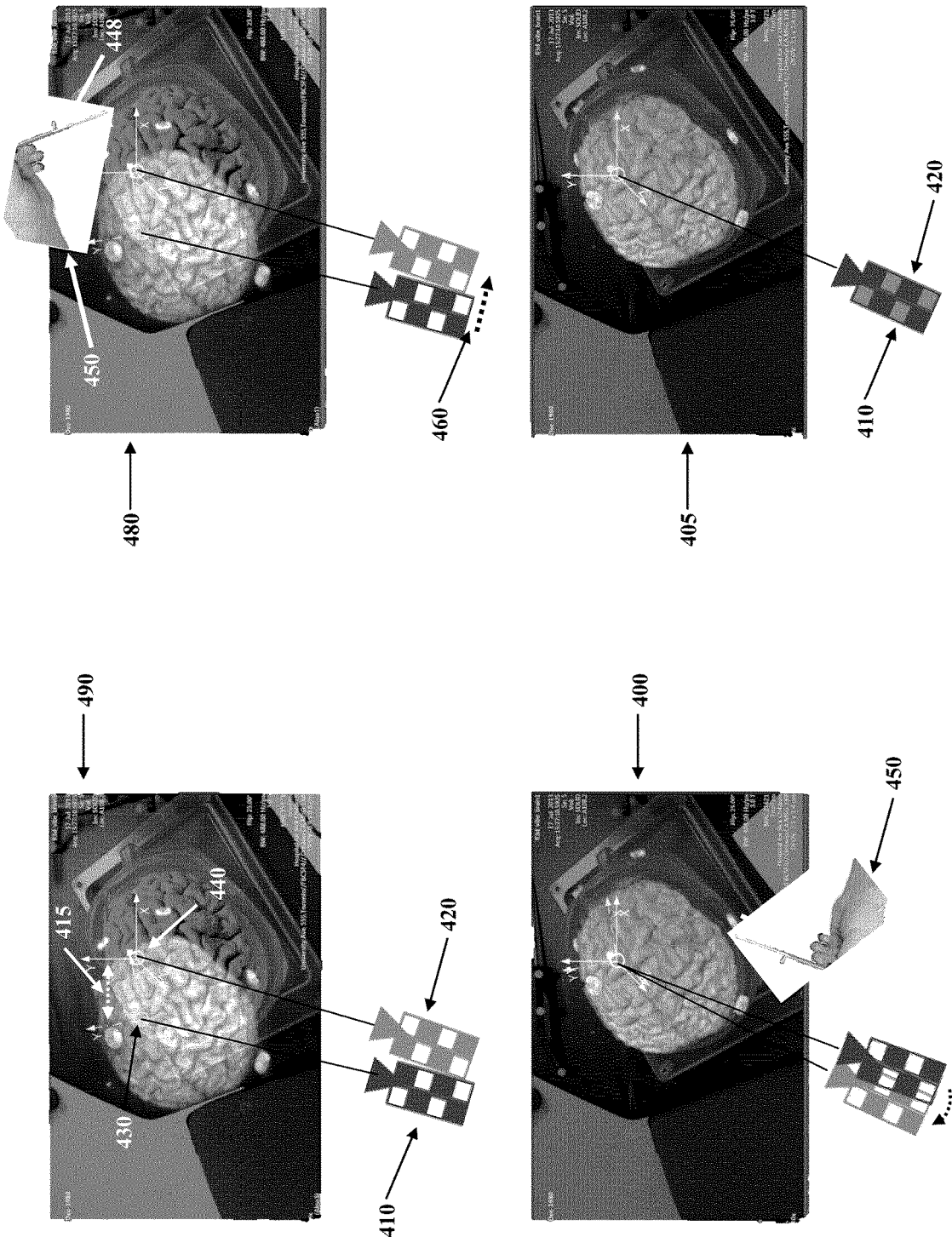
FIG. 4 is a diagram illustrating the registration of virtual and actual coordinate frames in an example navigation system.

FIG. 4 shows an example of how, during use, the navigation system 200 may be operated to determine a coordinate frame 440, which contains the actual spatial locations of tracked elements (e.g., the mechanical arm 202, the access port 206, the introducer 210, the tracked pointer 220 and/or other pointing tools) in the operating room and their spatial relations to one another. Another example of such tracked elements may be a surgical real-time imaging camera such as the optical scope 204. This may be a moveable camera used for visualization of the surgical area of interest, a surgical volume of interest such as a brain, and/or medical instruments. A 3D virtual volume representing pre-operative image data of patient anatomy (e.g., obtained prior to the procedure using suitable imaging modalities such as MR or CT) may be provided to the navigation system 200, and may be displayed on one or more displays 205, 211. In some examples, the virtual volume may be acquired using a patient with attached fiducial markers (not shown). The fiducial markers may remain attached in place on the patient (or else their locations may have been marked on the patient) in a manner which persists through the registration step in order to register the pre-operative imaging data with the patient in the operating room.

For example, actual fiducial markers positioned on the patient's head may be virtually in the same position relative to the patient's virtual brain scan as the actual fiducial markers relative to the patient's actual brain. The spatial correspondence between the actual fiducial markers and the virtual fiducial markers permits the actual and virtual coordinate frames to be aligned, which allows for an accurate overlay of virtual image data onto the actual image data.

This overlay of images may be achieved by combining video from a virtual camera 410 depicting the virtual operating room (OR) surgical field and video from an actual surgical imaging camera 420 depicting the actual OR surgical field. To obtain an accurate overlay, the two cameras 410, 420 should be coincidentally aligned and have substantially the same optical properties. Hence the alignment of the virtual camera 410 in a virtual coordinate frame 430 (defined in the navigation system 200) may be constrained to be equivalent to the alignment of the actual camera 420, relative to the actual coordinate frame 440 of the operating room, and have the same optical properties as the actual camera 420, namely, the same field-of-view, aspect ratio, and optical distance. This may be accomplished using the navigation system 200. Given an initial discrepancy or spatial separation 415 between the coordinate frames 430, 440, the tracked pointer 220 controlled by a user 450 (e.g., a surgeon 101) may be used to confirm the spatial location of the actual fiducial markers in virtual space as depicted in a picture frame 480 shown in the upper right hand side in FIG. 4.

In general, each time a point is identified, the virtual and actual coordinate frames 430, 440 become more accurately aligned. For example, as the tip of the tracked pointer 220 indicates the spatial position of a fiducial marker in actual space (in this example, located above the left eyebrow of the patient), its virtual counterpart fiducial marker aligns with it resulting in the navigation system virtual coordinate frame 430 to transform 460 and align its origin with the operating room actual coordinate frame 440. This also results in the two cameras 410, 420 realigning themselves accordingly. It should be noted that the relative shift in alignment of the cameras 410, 420, an example of which is shown between diagrams 490 and 400, may be proportional to the shift between the virtual alignment of the overlay on the actual image data between diagrams 490 and 400.

In some examples, the coordinate frames 430, 440 may be still rotationally misaligned, as illustrated in the example bottom left picture frame 400 in FIG. 4. Accordingly, the alignment process may be repeated and another point is registered. In this example iteration the fiducial marker being aligned is located near the right ear of the patient and this causes a rotation of the virtual coordinate frame 430, resulting in it and the actual coordinate frame 440 to better coincidently align.

Repetition of the above steps results in the production of a common coordinate frame, and accurate registration, as can be seen in diagram 405 (in the lower right hand side of FIG. 4) which shows the accurate overlay of the virtual and actual brain as a result of the coincident alignment of the virtual and actual cameras 410, 420, respectively.

Figure 5:
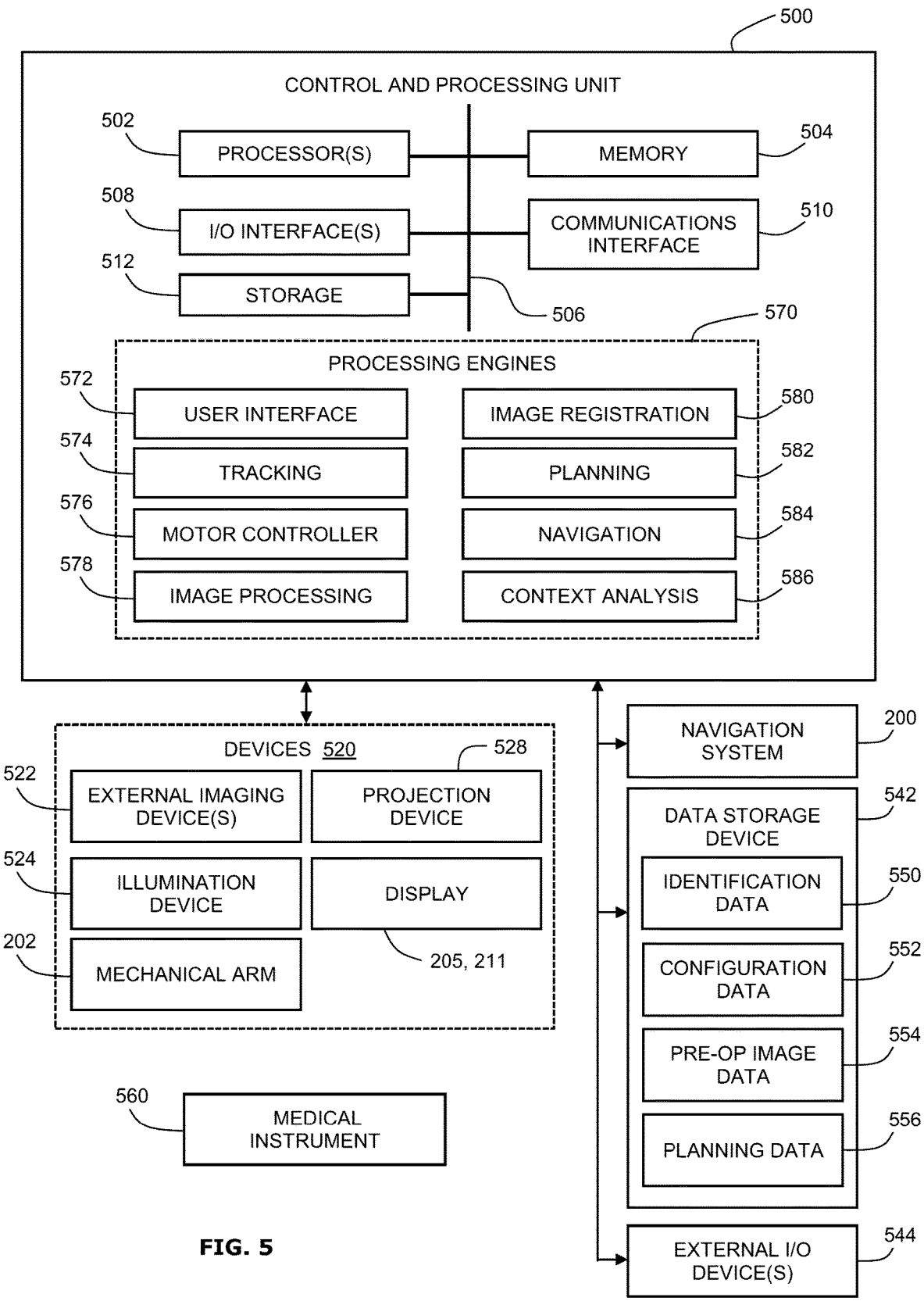
FIG. 5 shows a block diagram of an example system configuration, including a control and processing unit and external components.

FIG. 5 shows a block diagram of an example system configuration that may be used to carry out the functions of a planning system and/or a navigation system (with modifications as appropriate), as disclosed herein. The example system may include a control and processing unit 500 and other external components. In some examples, the same control and processing unit 500 may be used for both planning and navigation. In other examples, different instances of the control and processing unit 500 may be used for planning and navigation.

In some examples, the control and processing unit 500 may include one or more processors 502 (for example, a CPU and/or microprocessor), one or more memories 504 (which may include random access memory (RAM) and/or read-only memory (ROM)), a system bus 506, one or more input/output interfaces 508 (such as a user interface for a user (e.g., a surgeon) to provide various inputs (e.g., to perform trajectory planning or run simulations)), one or more communications interfaces 510, and one or more internal storage devices 512 (e.g. a hard disk drive, compact disk drive and/or internal flash memory). The control and processing unit may also include a power supply (not shown).

The control and processing unit 500 may interface with one or more other external devices, such as a tracking system or navigation system (e.g., the navigation system 200 of FIG. 2), a data storage device 542, and external input and/or output devices 544 which may include, for example, one or more of a display, keyboard, mouse, foot pedal, microphone and speaker. The data storage device 542 may include any one or more suitable data storage devices, such as a local or remote computing device (e.g., a computer, a hard drive, a digital media device, or a server) which may have a database stored thereon.

When used for intra-operative navigation, the data storage device 542 may store identification data 550 for identifying one or more medical instruments 560 and configuration data 552 that may associate customized configuration parameters with the one or more medical instruments 560. The data storage device 542 may also store preoperative image data 554 and/or medical procedure planning data 556. Although the data storage device 542 is shown as a single device, the data storage device 542 may be provided as one or more storage devices.

The medical instrument(s) 560 may be identifiable by the control and processing unit 500. The medical instrument(s) 560 may be connected to, and controlled by, the control and processing unit 500, or may be operated or otherwise employed independently of the control and processing unit 500. The navigation system 200 may be employed to track one or more of the medical instrument(s) 560 and spatially register the one or more tracked medical instruments 560 to an intra-operative reference frame, for example as discussed above.

The control and processing unit 500 may also interface with one or more other configurable devices 520, and may intra-operatively reconfigure one or more of such device(s) 520 based on configuration parameters obtained from configuration data 552, for example. Examples of the device(s) 520 may include one or more external imaging devices 522, one or more illumination devices 524, the mechanical arm 202, one or more projection devices 528, and one or more displays 205, 211.

Various embodiments and aspects of the present disclosure may be implemented via the processor(s) 502 and/or memory(ies) 504. For example, one or more of the functionalities and methods described herein may be at least partially implemented via hardware logic in the processor(s) 502 and/or at least partially using instructions stored in the memory(ies) 504, as one or more processing engines 570 (also referred to as modules). Example processing engines 570 include, but are not limited to, a user interface engine 572, a tracking engine 574, a motor controller 576, an image processing engine 578, an image registration engine 580, a procedure planning engine 582, a navigation engine 584, and a context analysis engine 586. Although certain engines (or modules) are described, it should be understood that engines or modules need not be specifically defined in the instructions, and an engine or module may be used to implement any combination of functions.

It is to be understood that the system is not intended to be limited to the components shown in FIG. 5. For example, one or more components of the control and processing unit 500 may be provided as an external component or device. Although only one of each component is illustrated in FIG. 5, any number of each component can be included. For example, a computer typically contains a number of different data storage media. Furthermore, although the bus 506 is depicted as a single connection between all of the components, the bus 506 may represent one or more circuits, devices or communication channels which link two or more of the components. For example, in personal computers, the bus 506 may include or may be a motherboard.

In some examples, the navigation engine 584 may be provided as an external navigation system that may interface with or be integrated with the control and processing unit 500.

Some embodiments or aspects of the present disclosure may be implemented using the processor 502 without additional instructions stored in the memory 504. Some embodiments or aspects of the present disclosure may be implemented using instructions stored in the memory 504 for execution by one or more general purpose microprocessors. In some examples, the control and processing unit 500 (which may be also referred to as a computer control system) may be, or may include, a general purpose computer or any other hardware equivalents configured for operation in space. The control and processing unit 500 may also be implemented as one or more physical devices that may be coupled to the processor(s) 502 through one or more communications channels or interfaces. For example, the control and processing unit 500 may be implemented using application specific integrated circuits (ASIC). In some examples, the control and processing unit 500 may be implemented as a combination of hardware and software, such as where the software may be loaded into the processor(s) 502 from the memory(ies) 504 or internal storage(s) 512, or from an external source (e.g., via the communication interface(s) 510, such as over a network connection). Thus, the present disclosure is not limited to a specific configuration of hardware and/or software.

Figure 6:
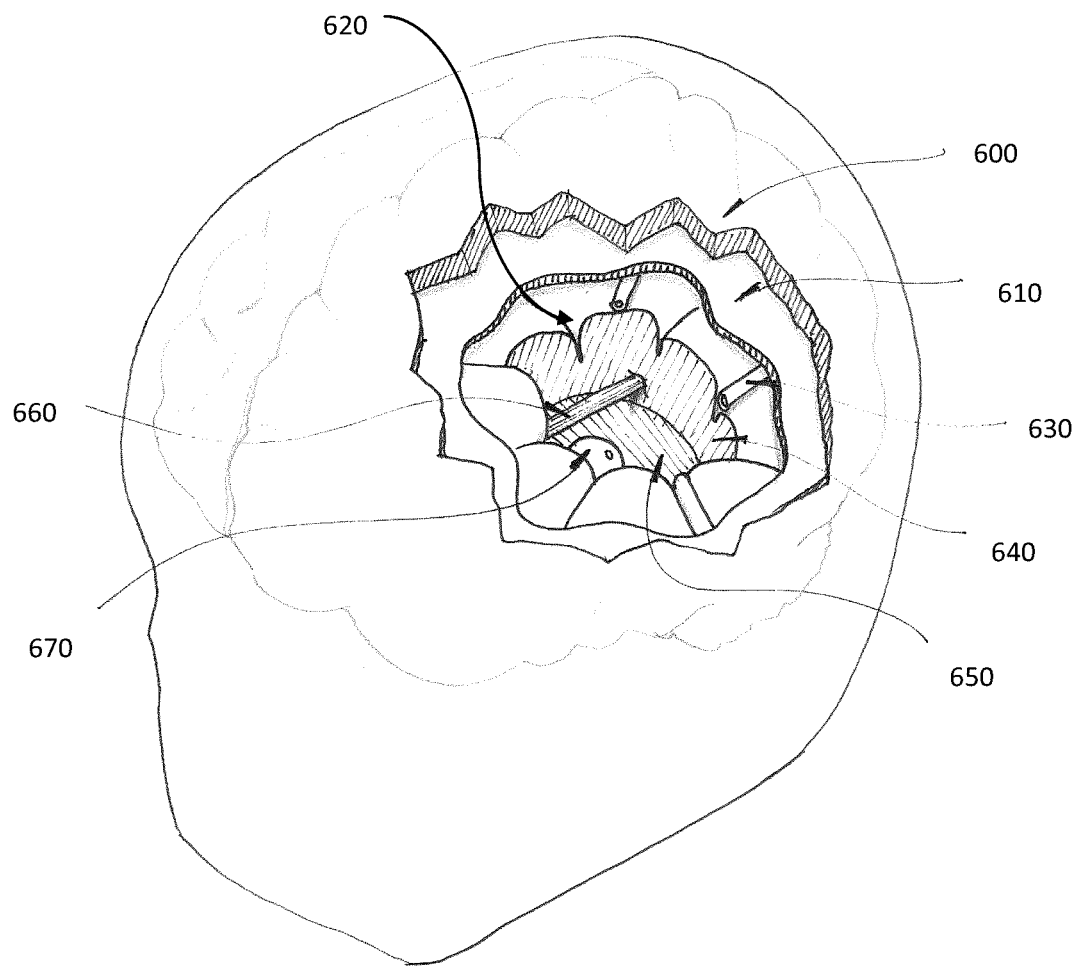
FIG. 6 is a diagram illustrating the layers of tissue encountered during a craniotomy procedure.

FIG. 6 illustrates the tissues that may be encountered during the port-based surgery. As illustrated, the tissues may include a skull 600, a dural layer 610 (or dura), a cerebro-spinal fluid (CSF) layer 620, blood vessels 630, and a brain section including grey matter 640, white matter 650, diffusion or brain fibers 660, and a tumor target 670.

FIG. 7A is a flow chart outlining an example method 700 for fabricating an artificial bone flap. FIG. 7B shows further details of the method 700. The method 700 may be carried out within the context of the navigation system 200, as described above. Although the surgeon 101 is described as being the principle operator in the method 700, a nurse or other operator 103 may alternatively or additionally be involved in carrying out the method.

At 710, a reference image of at least a portion of the patient's skull may be obtained. The reference image may be a pre-operative image or may be obtained during the procedure (but prior to performing the craniotomy). The reference image is typically a 3D image, which may be obtained using a MR or CT imaging system, or the 3D scanner 222. The reference image may be obtained using suitable techniques to image the patient's bone. For example, an appropriate pulse sequence may be selected for MR image acquisition, in order to capture bone tissue. In some examples, ultrashort echo time (UTE) MRI methods may be used to image the patient's bone. Where the reference image is a MR or CT image, the reference image may be obtained pre-operatively, for example prior to the process illustrated in FIG. 3A, and the reference image may additionally be used for planning the procedure. In the case of a 3D surface scan using the 3D scanner 222, the reference image may be obtained after the patient has been prepped (e.g., after the patient's hair has been shaved in the required region or after the skull has been exposed) but before performing the craniotomy. The reference image may be used to capture the shape of the skull bone prior to craniotomy.

The reference image may capture one or more fiducial markers positioned at relatively fixed positions on the patient's head or skull. Such fiducial markers may remain in place during the length of the procedure, to ensure proper registration of virtual and actual coordinate systems, as described above. In some examples, fiducial markers may be placed during on the patient's exposed skull in the vicinity of the planned craniotomy. Fiducial markers placed directly on the exposed skull may be captured by a 3D surface scan using the 3D scanner 222. By placing fiducial markers directly on the exposed skull, unwanted shifting of the fiducial markers due to movement of the patient's skin may be avoided.

The reference image may be used (at 710 or later in the method 700) to determine the curvature and thickness of the skull at the site of the craniotomy. Where such reference image is lacking in quality or missing, alternative methods, such as those described further below, may be used to infer curvature of the skull at or around the craniotomy location.

The craniotomy may be performed, and at 720 intra-operative data of the craniotomy opening may be obtained. Obtaining the intra-operative data may include obtaining 3D image data 750, obtaining a set of points defining a boundary of the craniotomy 760 and/or obtaining 2D image data 770.

At 750, obtaining 3D image data of the craniotomy may include obtaining a 3D surface scan of the craniotomy, such as by using a portable 3D scanner 222 or using optical coherence tomography (OCT) imaging (e.g., using a remotely operated robotically guided OCT system). Typically, OCT imaging may allow the imaging of surface structures and sub-surface structures up to a limited depth (e.g., around 3 mm), and at a relatively high resolution. A method for obtaining OCT surface images may involve the use of steerable mirrors to scan a beam of light across the surface being imaged; however, the scanned area is often a maximum of 1 cm$^2$, which is too small to cover the full area of a typical craniotomy. The surface area covered by the OCT scan may be increased by systematically moving the scanning head of the OCT system (e.g., using a robotic system to ensure precise and systematic movement), obtaining individual scans at each position, and then combining the small scanned areas together to form a larger surface map. A surface scan obtained using OCT in this way would also contain information about sub-surface structures up to the limited depth permitted by OCT. The 3D image data may capture the positions of the fiducial markers on the patient, to enable the captured intra-operative data to be related to the reference image obtained at 710. The 3D image data may capture the size, shape and depth of the skull opening created by the craniotomy.

At 760, data defining a boundary of the craniotomy may be obtained as a set of points along the boundary of the craniotomy. For example, the boundary may be defined by the surgeon 101 manually touching points or tracing along the border of the craniotomy directly on the patient's skull using a tracked pointer 220. By tracking and storing a series of positional data of the tip of the tracked pointer 220 during the tracing, a series of points defining the border of the craniotomy may be obtained. While touching or tracing the border of the craniotomy, the positional data of the tip of the tracked pointer 220 may be automatically tracked and stored (e.g., at regular time intervals, such as every 500 ms) by the navigation system 200. Alternatively, the surgeon 101 may manually trigger the storage of positional data at each touched point.

The tracked pointer 220 may also be used to indicate the thickness of the skull (e.g., by collecting positional data at points on the outer and inner edges of the craniotomy) and/or may also be used to indicate the curvature of the exposed dura (e.g., by collecting positional data at points on various locations on the dura). In some examples, this data may be used to approximate the thickness and/or curvature of the artificial bone flap to be fabricated.

In some examples, after a set of points defining the boundary of the craniotomy has been obtained, the surgeon 101 may provide input to the computer or control unit to indicate that the set of data is complete. The computer or control unit may then verify the collected data for consistency and completeness (e.g., perform algorithms to verify that the boundary forms a closed loop, that the boundary falls within the planned craniotomy and/or that the boundary does not deviate significantly from the planned craniotomy) and may cause the defined boundary to be displayed (e.g., overlaid on a 2D image on the display 205, 211) for confirmation by the surgeon 101. In some examples, such verification and/or feedback may be provided to the surgeon 101 during the obtaining of the set of points, to inform the surgeon 101 whether more points are needed or whether a sufficient number of points has been obtained.

At 770, obtaining 2D image data of the craniotomy may include obtaining a 2D optical image or video of the craniotomy, such as using the optical scope 204. The 2D image data may capture the position of the fiducial markers on the patient, to enable the captured intra-operative data to be related to the reference image obtained at 710.

At 772, a boundary of the craniotomy may be determined in the 2D image. For example, the boundary may be determined by manually defining the boundary in a captured 2D image. The 2D image may be displayed on the display 205, 211 and the surgeon 101 may use mouse input or touch-screen input, for example, to draw or trace the boundary of the craniotomy as shown in the 2D image. Alternatively or as an additional verification, the computer or control unit may perform an automatic edge detection algorithm to determine the boundary of the craniotomy as displayed in the 2D image.

In some examples, after the boundary of the craniotomy has been defined in the 2D image, the surgeon 101 may provide input to the computer or control unit to indicate that the input is complete. The computer or control unit may then verify the data for consistency and completeness (e.g., verify that the boundary forms a closed loop, that the boundary falls within the planned craniotomy and/or that the boundary does not deviate significantly from the planned craniotomy) and may display the defined boundary (e.g., overlaid on the 2D image on the display 205, 211) for confirmation by the surgeon 101.

In some examples, obtaining intra-operative data of the opening at 720 may include verification that the measured opening matches the planned craniotomy (e.g., as planned at 314 in FIG. 3A). If the intra-operative data indicates a location, size and/or shape of the craniotomy that deviates from the planned craniotomy by more than a predetermined amount (e.g., a difference of more than 1 cm) a warning or notification may be generated (e.g., as a visual display on the display 205, 211) indicating that the intra-operative data may be inaccurate or that the craniotomy may differ significantly from the plan.

At 730, the dimensions of the opening may be calculated based on the reference image and the intra-operative data. Where the intra-operative data has not been registered with the reference image, a registration of the intra-operative data and the reference image may be carried out as part of block 730. The intra-operative data may be compared against the reference image to determine the size, shape, thickness and/or curvature of the bone flap that was removed to create the opening.

Where the intra-operative data includes 3D image data (e.g., as obtained at 750), calculating the dimensions of the opening may include registering the 3D image data to the reference image (at 756) and comparing the 3D image data to the reference image (at 758).

At 756, registration of the 3D image data to the reference image may include identifying fiducial markers captured in each of the 3D image and the reference image and registering the fiducial markers of each image to each other, using suitable registration techniques.

At 758, the registered 3D and reference images may then be compared against each other to determine the portion of the skull (in the reference image) that was cut to form the opening (in the 3D image). For example, the 3D image may be subtracted from the reference image in order to obtain the portion of the skull that was cut to form the opening.

Where the intra-operative data includes a set of points defining a boundary of the opening (e.g., as obtained at 760), calculating the dimensions of the opening may include determining the boundary defined by the set of points (at 764), registering the boundary to the reference image (at 766) and determining the dimensions of the skull (in the reference image) that falls within the boundary (at 768).

At 764, determining the boundary defined by the set of points may be carried out using suitable algorithms for connecting the points to generate a relatively smooth, closed loop. Example mathematical algorithms for defining such boundary include cubic spline routines and polynomial functions in 3D space. The surface of the skull may be also incorporated using spline surfaces, which are smooth surfaces with defined curvature and boundary. In other words, the spline surface may be a mathematical model of the removed bone flap. This may be carried out using the computer or control unit in the navigation system. Determining the boundary may include quality assurance checks. For example, the computer or control unit may verify that there are a sufficient number of points to generate a smooth, closed loop, that the boundary falls within the planned craniotomy and/or that the boundary does not deviate significantly from the planned craniotomy. One or more of these quality assurance checks may also be carried out while obtaining the set of points at 760, and feedback may be provided to the surgeon 101 during the obtaining, to indicate whether more points are needed.

At 766, the determined boundary may be registered to the reference image by relating the location of the set of points to the reference image in the virtual coordinate system. Since the set of points may be obtained using the tracked pointer 222, the location of each point may already be defined in the virtual coordinate system. Using the known virtual coordinates of fiducial markers in the reference image, the determined boundary may be registered to the reference image. In some examples, registration of the set of points to the reference image may take place before determining the boundary. Registering the set of points to the reference image before determining the boundary may be useful for performing quality assurance checks.

At 768, the dimensions of the skull within the boundary may be determined by determining the dimensions (including skull thickness and curvature, for example) of the reference image that is bounded by the registered boundary.

Where the intra-operative data includes 2D image data and a boundary determined in the 2D image data (e.g., as obtained at 770 and 772), calculating the dimensions of the opening may include registering the 2D image data to the reference image (at 776) and determining the dimensions of the skull (in the reference image) that falls within the boundary (at 778).

At 776, registering the 2D image data to the reference image may include identifying fiducial markers captured in each of the 2D image and the reference image and registering the fiducial markers of each image to each other, using suitable registration techniques. Once the 2D image is registered with the reference image, the boundary determined in the 2D image (at 772) may be automatically registered to the reference image.

At 778, determining the dimensions of the skull within the boundary may include determining the dimensions (including skull thickness and curvature, for example) of the reference image that is bounded by the registered boundary. Where such reference image is lacking in resolution or missing, it may be augmented by interpolating the intra-operative 3D scan of the intact portion of the skull or head to infer the curvature of the removed bone flap piece. This interpolation may be performed, for example, by creating a mathematical grid to represent the entire head using the intact portion of the head. Then, assuming that the head surface, and hence the skull surface, is relatively smooth, the surface grid may be interpolated over the bone flap region to arrive at a "filled in" model. The latter information may then be used to represent the curvature of the bone flap surface.

At 740, the calculated dimensions for fabricating the artificial bone flap may be provided. This may include providing data suitable for use by a fabrication system, for fabricating the artificial bone flap. The calculated dimensions may be transmitted to the fabrication system in the form of data signals (e.g., through wired or wireless communication) or may be provided in a tangible form (e.g., a storage medium such as a computer readable memory) to be manually transferred to the fabrication system.

In some examples, the computer or control unit may carry out further processing of the dimensions before providing the dimensions to a fabrication system. For example, the calculated dimensions of the opening may be provided in the form of a digital 3D model of the artificial bone flap that is to be fabricated. In some examples, the 3D model may be only for a portion of the removed bone flap, such as a remaining portion of the natural bone flap has been preserved. This may be useful where only a portion of the natural bone flap could be salvaged. This approach may help with bone regeneration and patient healing, as part of the living tissue is reused.

In some examples, the calculated dimensions may be used to facilitate selection and/or cutting of a segment of an artificial dura (e.g., made of a synthetic or biological material) which may be used to close the open dura in the patient. In some examples, the calculated dimensions may help in selection of an artificial dura from a pre-existing inventory of differently-sized artificial duras. The cutting of a segment of the artificial dura (either cutting the artificial dura from a large piece of material or trimming of a pre-sized piece of material) may be guided by a boundary that is optically projected on to the cutting surface. The projected boundary may be generated based on the calculated dimensions provided at 740. Example techniques for projecting a boundary on the artificial dura include a laser dot that is moved reasonably swiftly over the surface of the artificial dura to generate a cutting track or an image directly projected on the cutting surface using projected light from a fixed distance, for example.

In some examples, the computer or control unit may, in addition to the calculated dimensions, provide scaled versions (e.g., 95% or 90%) of the calculated dimensions, in order to fabricate one or more artificial bone flaps that are slightly smaller than the actual calculated dimensions of the craniotomy. Fabricating the artificial bone flap to be slightly smaller than the calculated dimensions of the opening may be useful to provide a margin of error (e.g., to accommodate possible errors in determining the boundary of the craniotomy) when fitting the artificial bone flap into the opening. A slightly smaller artificial bone flap may also provide a small gap between the perimeter of the artificial bone flap and the patient's skull, into which bonding substances and devices (e.g., bio-adhesives, sutures, plates and/or wires) may be introduced to aid in healing.

The calculated dimensions may be provided (e.g., as a digital model) as input to a fabrication system for additive or subtractive 3D manufacturing. Any suitable rapid prototyping system may be used to fabricate the artificial bone flap. Additive 3D manufacturing may also be referred to as 3D printing and may include various suitable manufacturing techniques including extrusion deposition, binding of granular materials, laminated object manufacturing, or photopolymerization, among others. Subtractive 3D manufacturing may include techniques such as etching, cutting or drilling, among others. The fabrication of the artificial bone flap may be relatively fast (e.g., being complete in time for the artificial bone flap to be used to close the craniotomy at the end of the procedure), such as within less than 30 minutes. Where the fabrication technique is suitably fast, multiple artificial bone flaps may be manufactured while the procedure is still ongoing.

The calculated dimensions may be also used to facilitate selection of an artificial bone flap from a pre-existing inventory of differently-sized artificial bone flaps. For example, artificial bone flap replacement components may be purchased in different predefined sizes. The calculated dimensions may aid in selecting the desired predefined size that meets the needs of a particular procedure. Further, after the artificial bone flap has been selected from predefined sizes, the calculated dimensions may be further used to trim or otherwise shape (e.g., by manually bending or shaping a bone mesh) the pre-sized artificial bone flap to meet the exact dimensional requirements for the procedure.

In some examples, where the pre-existing artificial bone flap has been pre-selected pre-operatively (e.g., according to the example method 1000 discussed above), the calculated dimensions may be used to guide modification (e.g., trimming and/or manually shaping) of the pre-selected artificial bone flap. For example, the 3D dimensions of the pre-selected artificial bone flap (e.g., obtained by performing a 3D scan of the artificial bone flap or obtained by looking up the dimensions from a catalogue or database) may be compared against the calculated dimensions of the bone opening, and any differences may be the basis of guidance for modifying the pre-selected artificial bone flap to better conform to the 3D dimensions of the bone opening.

Where different sizes of artificial bone flaps have been pre-selected, the calculated dimensions may be used to guide selection of which one artificial bone flap should be used.

In some examples, the fabricated artificial bone flap may be used to help shape (e.g., bend) other materials that will also be used to close the cranial opening. For example, the artificial bone flap may serve as a guide to help bend mesh-like cranial opening covers so that the mesh structures closely match the curvature that is present on the head surface in the vicinity of the cranial opening.

The artificial bone flap may be fabricated using any suitable biocompatible material. In some examples, the artificial bone flap may be fabricated to be relatively porous, to assist in bone growth and patient healing. Examples of suitable materials include calcium phosphate, polyethylene, bioactive glass and demineralized bone. Other materials may be used. Details of the suitability of various materials are presented in "Reconstruction of Skull Defects: Currently Available Materials," Goiato et. al., J Craniofac Surg 2009; 20: 1512-1518, which is hereby incorporated by reference.

In some examples, more than one artificial bone flap may be fabricated. The plurality of artificial bone flaps may be identical or may be different in material and/or dimensions. For example, different artificial bone flaps may be fabricated using different materials (e.g., selected among a variety of suitable biocompatible materials), which may be useful to enable the surgeon to select the artificial bone flap having a desired material property (e.g., stiffness) to suit the patient. Different artificial bone flaps may also be fabricated with different dimensions. For example, several artificial bone flaps may be fabricated at 100%, 90% and 80% of the size of the calculated dimensions. By providing a variety of sizes, the surgeon may be able to select the artificial bone flap that accommodates a desired bonding method and/or best fits the actual craniotomy opening. The fit of a fabricated artificial bone flap may be assessed by holding the artificial bone flap in the field of view of the camera system used at 770. The image processing system used to estimate the profile and dimensions of the craniotomy may be used to estimate similar information for the artificial bone flap. The computed profile and dimensions of the artificial bone flap may be then automatically compared to those of the craniotomy to confirm that the artificial bone flap will fit the craniotomy opening without having to actually place the fabricated bone flap on the opening.

The artificial bone flap may then be used to close the craniotomy, using suitable techniques, instead of the original bone flap removed to create the craniotomy.

As discussed above, in some aspects of the present disclosure, selection, modification and/or fabrication of an artificial bone flap may be guided by feedback provided during pre-operative planning. Such a function may be integrated into a planning system, such as the system described in PCT application no. PCT/CA2014/050272, titled "PLANNING, NAVIGATION AND SIMULATION SYSTEMS AND METHODS FOR MINIMALLY INVASIVE THERAPY", previously incorporated by reference. It should be understood that such guidance and feedback may be provided only pre-operatively, only intra-operatively, or throughout both pre-operative and intra-operative stages.

In some examples, the present disclosure enables automated feedback for selection of an artificial bone flap to be provided during planning of a surgical procedure. This may be useful to simplify the selection of artificial bone flaps and increase efficiency. Further, the automated feedback may take into consideration factors such as bone density and structural integrity in the vicinity of the bone opening, using calculations based on pre-operative image data. Such consideration may not be possible in conventional manual selection of artificial bone flaps.

In some examples, the present disclosure enables an artificial bone flap to be fabricated, for example while a neurosurgery is ongoing. The measurement, fabrication and completion of the artificial bone flap may all take place during the procedure, and in near real-time, in parallel with the procedure. Thus, the artificial bone flap can be customized to the specific craniotomy created and be available to close the craniotomy at the end of the procedure.

Obtaining a reference image (e.g., a MR or CT image) of the patient's skull is typically already performed as part of pre-operative planning, and obtaining intra-operative data of the craniotomy opening may be relatively simple and quick (e.g., obtaining a 3D image using a portable 3D scanner). Thus, the present disclosure may be implementable in standard neurosurgery with relatively little impact on the length and/or complexity of the procedure.

In some examples, the present disclosure may be used to create an artificial bone flap to close a skull opening for a patient on whom a craniectomy was previously performed. This may be useful for cases where the original bone flap may be no longer available or where preserving the original bone flap for an extended period of time may be problematic. In some examples, larger portions of the skull may be artificially fabricated for the purpose of maxiofacial reconstruction. The present disclosure may also be adapted to fabricate vertebral components or bodies for the purpose of reconstructive surgery of the spine.

In some examples, the present disclosure may be implemented in addition to or as a backup for conventional procedures that use the patient's original bone flap to close the craniotomy. For example, the artificial bone flap may be selected or fabricated as a backup in case the original bone flap is or becomes unsuitable for closing the craniotomy (e.g., the original bone flap is or becomes damaged or contaminated). Though the present disclosure provides examples in the context of cranial surgery, the disclosed systems and methods may be applied to any other suitable procedure where a portion of the bone or rigid anatomical structure needs to be removed during a surgical procedure and then replaced at the conclusion of the procedure. Examples of such procedures include maxiofacial procedures and spinal procedures where portion of the spinal structure may be removed for subsequent replacement with real or artificial bone structure.

In some examples, information about the bone flap (and optionally bone fasteners), whether selected from existing available bone flaps or manufactured on-the-fly, may be stored for future use. For example, dimensions and/or model numbers of the parts used may be uploaded to a database or an informatics system. This information may be used for training purposes, to assist in future planning, to be shared with other hospitals or surgeons, atlased, or otherwise archived for future reference.

While some embodiments or aspects of the present disclosure may be implemented in fully functioning computers and computer systems, other embodiments or aspects may be capable of being distributed as a computing product in a variety of forms and may be capable of being applied regardless of the particular type of machine or computer readable media used to actually effect the distribution.

At least some aspects disclosed may be embodied, at least in part, in software. That is, some disclosed techniques and methods may be carried out in a computer system or other data processing system in response to its processor, such as a microprocessor, executing sequences of instructions contained in a memory, such as ROM, volatile RAM, non-volatile memory, cache or a remote storage device.

A computer readable storage medium may be used to store software and data which when executed by a data processing system causes the system to perform various methods or techniques of the present disclosure. The executable software and data may be stored in various places including for example ROM, volatile RAM, non-volatile memory and/or cache. Portions of this software and/or data may be stored in any one of these storage devices.

Examples of computer-readable storage media may include, but are not limited to, recordable and non-recordable type media such as volatile and non-volatile memory devices, read only memory (ROM), random access memory (RAM), flash memory devices, floppy and other removable disks, magnetic disk storage media, optical storage media (e.g., compact discs (CDs), digital versatile disks (DVDs), etc.), among others. The instructions can be embodied in digital and analog communication links for electrical, optical, acoustical or other forms of propagated signals, such as carrier waves, infrared signals, digital signals, and the like. The storage medium may be the Internet cloud, or a computer readable storage medium such as a disc.

Furthermore, at least some of the methods described herein may be capable of being distributed in a computer program product comprising a computer readable medium that bears computer usable instructions for execution by one or more processors, to perform aspects of the methods described. The medium may be provided in various forms such as, but not limited to, one or more diskettes, compact disks, tapes, chips, USB keys, external hard drives, wire-line transmissions, satellite transmissions, Internet transmissions or downloads, magnetic and electronic storage media, digital and analog signals, and the like. The computer useable instructions may also be in various forms, including compiled and non-compiled code.

At least some of the elements of the systems described herein may be implemented by software, or a combination of software and hardware. Elements of the system that are implemented via software may be written in a high-level procedural language such as object oriented programming or a scripting language. Accordingly, the program code may be written in C, C++, J++, or any other suitable programming language and may comprise modules or classes, as is known to those skilled in object oriented programming. At least some of the elements of the system that are implemented via software may be written in assembly language, machine language or firmware as needed. In either case, the program code can be stored on storage media or on a computer readable medium that is readable by a general or special purpose programmable computing device having a processor, an operating system and the associated hardware and software that is necessary to implement the functionality of at least one of the embodiments described herein. The program code, when read by the computing device, configures the computing device to operate in a new, specific and predefined manner in order to perform at least one of the methods described herein.

While the teachings described herein are in conjunction with various embodiments for illustrative purposes, it is not intended that the teachings be limited to such embodiments. On the contrary, the teachings described and illustrated herein encompass various alternatives, modifications, and equivalents, without departing from the described embodiments, the general scope of which is defined in the appended claims. Except to the extent necessary or inherent in the processes themselves, no particular order to steps or stages of methods or processes described in this disclosure is intended or implied. In many cases the order of process steps may be varied without changing the purpose, effect, or import of the methods described.

The invention claimed is:

1. A method of providing feedback to guide selection of an artificial bone flap and an artificial dura using a computer processor programmed with a set of instructions that, when executed, perform the method comprising:

providing a user interface for planning a neurosurgical procedure, the neurosurgical procedure comprising closing of an opening in a portion of a natural bone of a patient's skull and a portion of a patient's dura by respectively using the artificial bone flap and the artificial dura to be selected, the user interface in communication with the computer processor;

using the computer processor programmed with the set of instructions that, when executed:

determining 3D dimensions of the opening using at least pre-operative three-dimensional (3D) imaging data from a data storage device in communication with the programmed computer processor, the data storage device also storing the neurosurgical procedure planning data;

calculating at least one of: a bone density in a vicinity of the opening, and a bone structural integrity, as well as at least one dura dimension in the vicinity of the opening by using at least the pre-operative three-dimensional (3D) imaging data from the data storage device, thereby providing a calculation of at least one of: the bone density in the vicinity of the opening and the bone structural integrity, as well as the at least dura dimension in the vicinity of the opening;

determining one or more locations in the vicinity of the opening, using at least the pre-operative three-dimensional (3D) imaging data from the data storage device, suitable for attaching a bone flap fastener based on the calculation, thereby providing the one or more locations to preserve the natural bone structure and the patient's dura in the vicinity of the opening;

determining one or more parameters for selecting the artificial bone flap and the artificial dura for closing the opening based on the calculation and on the 3D dimensions of the opening, thereby providing the one or more parameters matching the natural bone structure and the patient's dura dimension, the artificial bone flap comprising a dimension smaller in relation to the opening, wherein a gap is provided between a periphery of the artificial bone flap and a periphery of opening in the patient's skull through which bonding substances and bonding devices are introduced to facilitate healing between the artificial dura and the patient's dura and to facilitate healing between the artificial bone flap and the natural bone of the patient's skull, the bonding substances comprising bio-adhesives, and the bonding devices comprising sutures; and using the computer processor programmed with the set of instructions that, when executed:

identifying the bone flap fastener based on the calculation for fixing the artificial bone flap to the natural bone over the opening; and providing output indicating one or more recommended available artificial bone flaps and one or more recommended available artificial dura suitable for closing the opening from the data storage device, based on the calculation, the determined one or more parameters and the determined one or more locations for attaching the bone flap fastener.

2. The method of claim 1, wherein the output indicating the one or more locations for attaching the bone flap fastener comprises a 2D or 3D image of the vicinity of the opening, one or more indications of the one or more locations being overlaid on the 2D or 3D image.

3. The method of claim 1, wherein the one or more parameters for selecting the artificial bone flap further comprise one or more of:
the bone density in a vicinity of the opening;
the bone structural integrity in the vicinity of the opening; and
the one or more locations for attaching the bone flap fastener.

4. The method of claim 1 wherein the one or more parameters for selecting the artificial bone flap further comprise one or more of:

bone thickness in the vicinity of the opening; and
a patient characteristic.

5. The method of claim 4 wherein the patient characteristic is one or more of:
patient age; and
patient sex.

6. The method of claim 1 wherein the pre-operative 3D imaging data comprise at least one of computer tomography (CT) data or magnetic resonance imaging (MRI) data.

7. The method of claim 1 wherein calculating the bone structural integrity in the vicinity of the opening comprises performing finite element analysis on the pre-operative 3D imaging data.

8. The method of claim 1, further comprising:
receiving input defining a boundary of the opening; and
calculating the 3D dimensions of the opening using the defined boundary.

9. The method of claim 8 wherein the input defining the boundary is at least one of:
a set of points positioned along a periphery of the opening;
a trace of a periphery of the opening; and
calculated dimensions determined based on a location of a target and a defined entry point of the neurosurgical procedure.

10. The method of claim 1, further comprising:
searching the database of available artificial bone flaps and artificial dura to respectively identify the one or more recommended available artificial bone flaps and or more recommended available artificial dura, by respectively determining one or more available artificial bone flaps and one or more recommended available artificial dura satisfying the one or more parameters; and
providing the output comprising identification of the one or more recommended available artificial bone flaps and the one or more recommended available artificial dura from the database.

11. The method of claim 1, further comprising:
after an artificial bone flap has been selected, obtaining 3D dimensions of the selected artificial bone flap;
comparing the 3D dimensions of the selected artificial bone flap to the determined 3D dimensions of the opening; and
providing further output indicating one or more recommended dimensional modifications to the selected artificial bone flap, based on any differences between the 3D dimensions of the selected artificial bone flap and the determined 3D dimensions of the opening.

12. The method of claim 11, wherein the further output comprises one or more recommendations for manually shaping the selected artificial bone flap to more closely approximate the calculated 3D dimensions of the opening.

13. The method of claim 11, further comprising:
using the computer processor programmed with the set of instructions that, when executed:
obtaining at least intra-operative 3D imaging data of at least the opening from an imaging system; and
determining, from the intra-operative 3D imaging data, intra-operative 3D dimensions of at least the opening,
wherein comparing comprises using the intra-operative 3D dimensions of at least the opening.

14. The method of claim 1, wherein the one or more fasteners comprises one or more of: a bone screw, a bone staple, and a bone adhesive.

* * * * *